(12) United States Patent
Fukuda et al.

(10) Patent No.: US 11,547,309 B2
(45) Date of Patent: Jan. 10, 2023

(54) BIOLOGICAL INFORMATION DETECTION DEVICE, BIOLOGICAL INFORMATION DETECTION METHOD AND NON-TRANSITORY COMPUTER-READABLE STORAGE MEDIUM FOR BIOLOGICAL INFORMATION DETECTION

(71) Applicant: HITACHI, LTD., Tokyo (JP)

(72) Inventors: Nobuhiro Fukuda, Tokyo (JP); Masashi Kiguchi, Tokyo (JP); Takashi Numata, Tokyo (JP); Hironori Wakana, Tokyo (JP)

(73) Assignee: Hitachi, Ltd.

( * ) Notice: Subject to any disclaimer, the term of this patent is extended or adjusted under 35 U.S.C. 154(b) by 301 days.

(21) Appl. No.: 16/818,189

(22) Filed: Mar. 13, 2020

(65) Prior Publication Data

US 2020/0337573 A1 Oct. 29, 2020

(30) Foreign Application Priority Data

Apr. 26, 2019 (JP) .............................. JP2019-084995

(51) Int. Cl.
*G06K 9/00* (2022.01)
*A61B 5/024* (2006.01)
(Continued)

(52) U.S. Cl.
CPC ........ *A61B 5/02416* (2013.01); *A61B 5/0261* (2013.01); *A61B 5/02108* (2013.01);
(Continued)

(58) Field of Classification Search
CPC ............ A61B 5/02416; A61B 5/02108; A61B 5/0261; A61B 5/441; A61B 5/7278;
(Continued)

(56) References Cited

U.S. PATENT DOCUMENTS 10,349,887 B1 * 7/2019 Tzvieli ................. A61B 5/6803
11,064,895 B2 7/2021 Onishi et al.
(Continued)

FOREIGN PATENT DOCUMENTS

JP 2015054223 A 3/2015
JP 2018-068431 A 5/2018
(Continued)

OTHER PUBLICATIONS

Japanese Office Action dated Nov. 15, 2022 for Japanese Patent Application No. 2019-084995.

*Primary Examiner* — Shervin K Nakhjavan
(74) *Attorney, Agent, or Firm* — Volpe Koenig

(57) ABSTRACT

A biological information detection device includes: a video capture unit, a blood flow analysis unit, a local pulse wave detection unit, a pulse wave propagation velocity calculation unit, and a blood pressure estimation unit. The video capture unit obtains video information on a face of a living body. The blood flow analysis unit analyzes video data of at least three skin areas in the video information, as blood flow information. The local pulse wave detection unit is provided for each skin area to calculate pulse information based on the blood flow information sequenced chronologically. The pulse wave propagation velocity calculation unit calculates a pulse wave propagation velocity based on a phase difference between pieces of the pulse information at each skin area calculated by the local pulse wave detection unit. The blood pressure estimation unit estimates blood pressure based on the pulse wave propagation velocity.

14 Claims, 14 Drawing Sheets

(51) Int. Cl.
*A61B 5/021* (2006.01)
*A61B 5/026* (2006.01)
*A61B 5/00* (2006.01)
*G06T 7/00* (2017.01)

(52) U.S. Cl.
CPC ............ *A61B 5/441* (2013.01); *A61B 5/7278* (2013.01); *G06T 7/0014* (2013.01); *A61B 2576/02* (2013.01); *G06T 2207/10016* (2013.01); *G06T 2207/30088* (2013.01); *G06T 2207/30104* (2013.01); *G06T 2207/30201* (2013.01)

(58) Field of Classification Search
CPC .............. A61B 2576/02; A61B 5/0077; A61B 5/02125; G06T 7/0014; G06T 2207/10016; G06T 2207/30088; G06T 2207/30104; G06T 2207/30201; G06T 7/0016; G06T 2207/10024
See application file for complete search history.

(56) References Cited

U.S. PATENT DOCUMENTS

| | | | |
|---|---|---|---|
| 2015/0374249 A1* | 12/2015 | Elliott | A61B 5/489 600/301 |
| 2016/0228011 A1* | 8/2016 | Tsubaki | A61B 5/024 |
| 2017/0164904 A1* | 6/2017 | Kirenko | G06T 7/0012 |
| 2018/0199870 A1* | 7/2018 | Lee | G16H 50/20 |
| 2019/0223737 A1* | 7/2019 | Tzvieli | A61B 5/02125 |

FOREIGN PATENT DOCUMENTS

| | | |
|---|---|---|
| JP | 2018-153555 A | 10/2018 |
| WO | 2018/088358 A | 5/2018 |

* cited by examiner

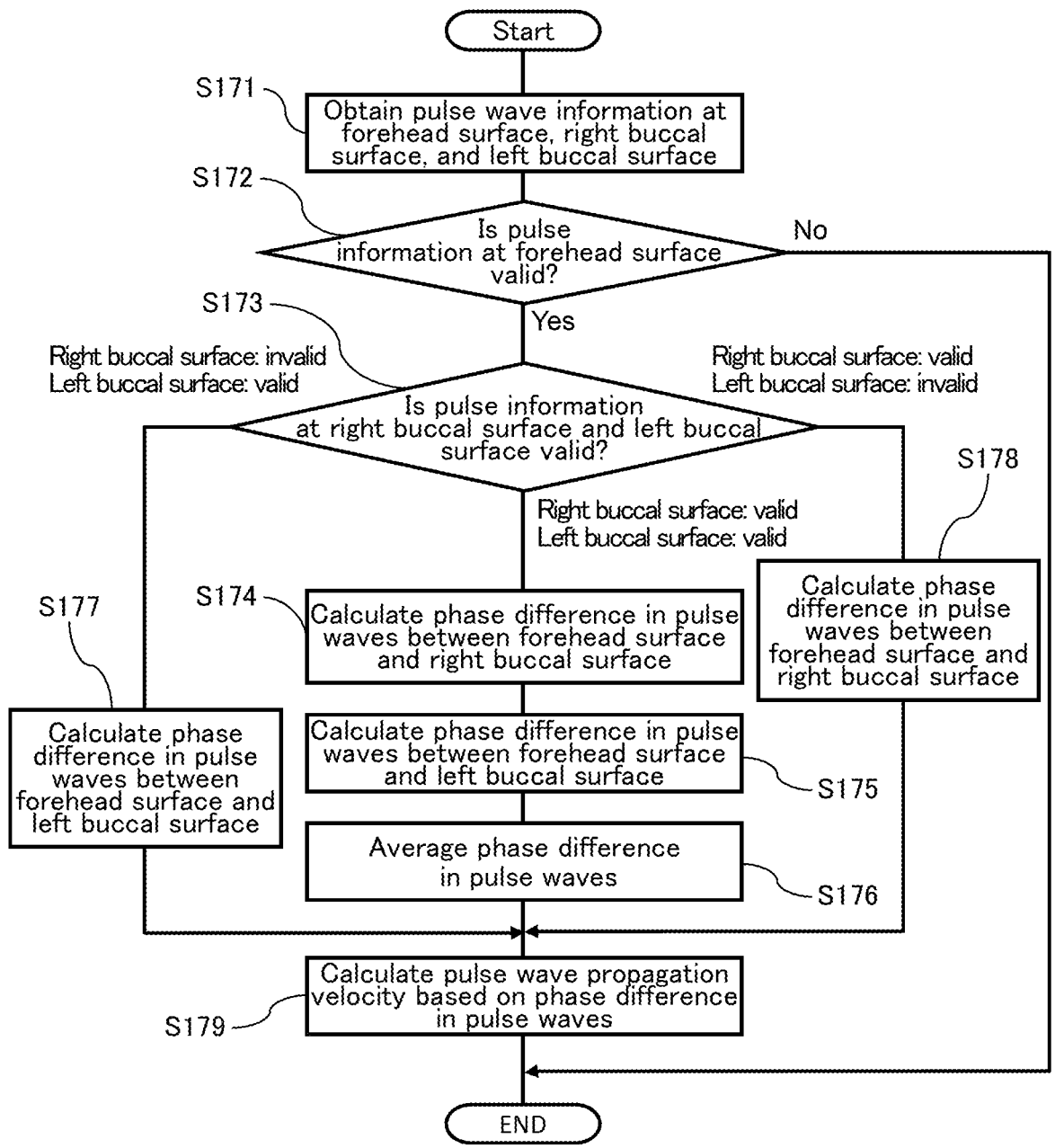

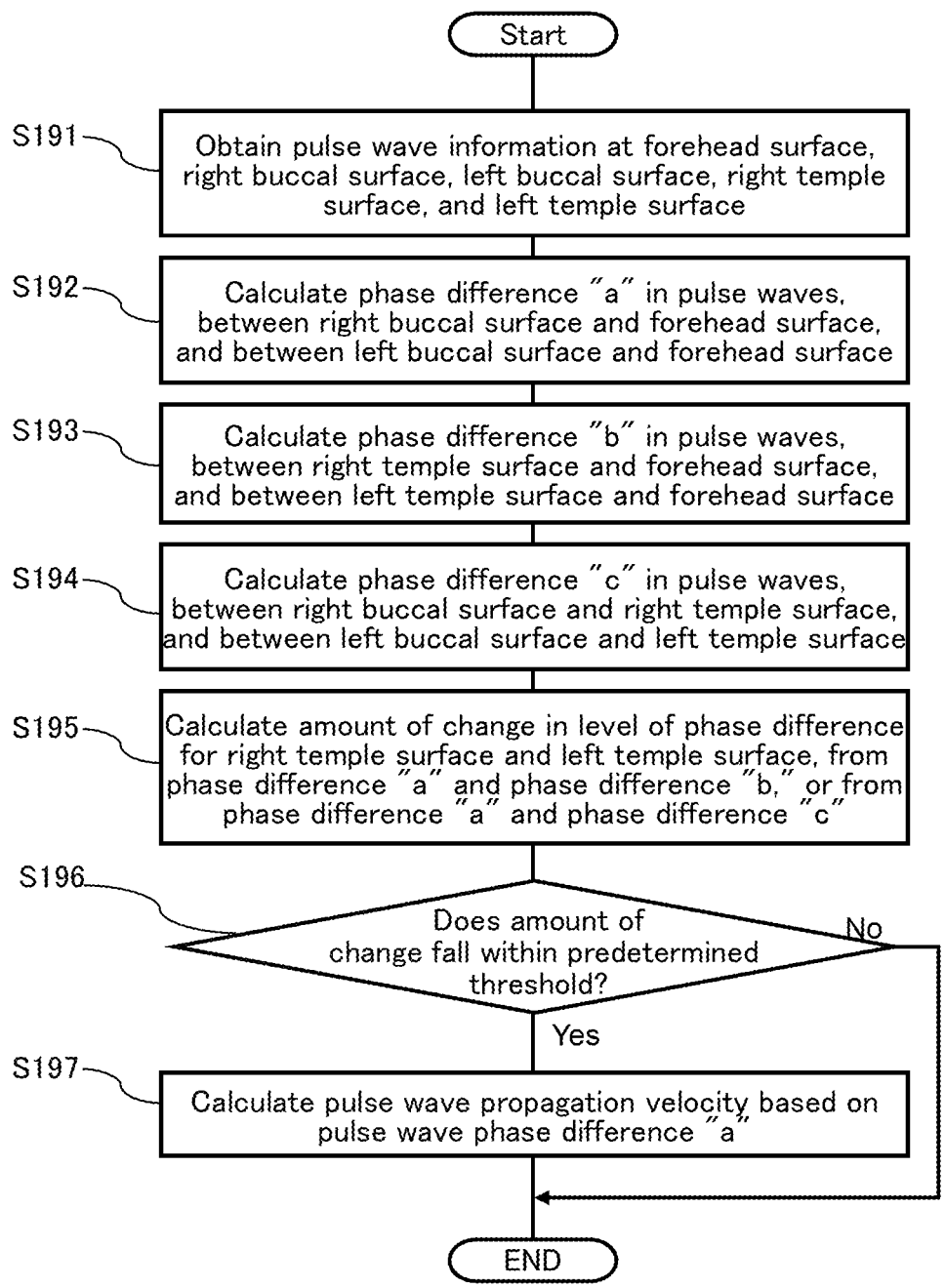

BIOLOGICAL INFORMATION DETECTION DEVICE, BIOLOGICAL INFORMATION DETECTION METHOD AND NON-TRANSITORY COMPUTER-READABLE STORAGE MEDIUM FOR BIOLOGICAL INFORMATION DETECTION

CROSS-REFERENCE TO RELATED APPLICATION

This application claims the benefit of priority to Japanese Patent Application No. JP2019-084995 filed on 26 Apr. 2019, the disclosures of all of which are hereby incorporated by reference in their entireties.

TECHNICAL FIELD

The present invention relates to a biological information detection device, a biological information detecting method and a non-transitory computer-readable storage medium for biological information detection, to detect biological information of a living body in real time in a non-contact manner.

BACKGROUND ART

Such a technique has been attracting attention in recent years that the dynamic state of a living body is detected in real time using a microwave or a camera in a non-contact manner. For example, a technique of detecting the heart rate and the like, based on the temporal change of a subject's face video obtained by a camera, has been mounted on mobile terminals such as smartphones, along with a camera module being reduced in size, and has rapidly become popular. In addition, the technique has been evolved into a technique of measuring the blood pressure of a subject in real time using a smartphone or the like.

Japanese Patent Application Publication No. 2015-054223 A (hereinafter referred to as Patent Document 1), for example, discloses a technique of detecting pulse wave signals, from an imaged video for two portions of a subject, at the respective portions, to obtain a pulse wave propagation velocity from the pulse wave signals at the two portions, and estimating a subject's blood pressure based on a Moens-Korteweg blood vessel model and the relationship between elasticity of a blood vessel wall and blood pressure.

SUMMARY OF THE INVENTION

Problems to be Solved

The technique disclosed in Patent Document 1 obtains respective pieces of pulse wave information from a video of the nose and fingertips of the living body, where the capillaries are concentrated, and calculates pulse wave propagation information based on a time difference between the pieces of pulse wave information, to estimate blood pressure information on the living body. Accordingly, the blood pressure is measured without a large pressure being applied to the living body, as compared with blood pressure measurement using a cuff (a measurement method in which a cuff wrapped around an arm is inflated by air pressure to apply a large pressure to the arm and blood pressure is measured based on the repulsion of a blood vessel in the arm), to allow for reducing the burden on a living body. However, in order to obtain the video information of the nose and fingertips of a living body, the technique requires the subject to take a predetermined posture and this is inconvenient.

The present invention is intended to provide a biological information detection device, a biological information detection method, and a non-transitory computer-readable media used for biological information detection, which give less burden on a subject and are convenient.

Solution to Problems

A biological information detection device of the present invention solves the above-identified problem and includes: a video capture unit to obtain video information having a face of a living body captured; a blood flow analysis unit to analyze video data of at least three skin areas in the video information, as blood flow information, inclusive of a skin area located on a center line of the face and a pair of skin areas, which is located bilaterally symmetric to the center line and has a blood flow path closer to the heart than the skin area located on the center line; a local pulse wave detection unit provided for each skin area to calculate pulse information at the skin area based on the blood flow information sequenced chronologically; a pulse wave propagation velocity calculation unit to calculate a pulse wave propagation velocity based on a phase difference between pieces of the pulse information at each of the skin areas calculated by the local pulse wave detection unit; and a blood pressure estimation unit to estimate blood pressure based on the pulse wave propagation velocity.

Advantageous Effects of the Invention

The present invention allows for obtaining biological information (blood pressure, pulse) with a small burden on the subject and with convenience.

BRIEF DESCRIPTION OF DRAWINGS

FIG. 17 is a flowchart of processing by a pulse wave propagation velocity calculation unit;

FIG. 19 is a flowchart of processing by the pulse wave propagation velocity calculation unit in a case where a pulse wave propagation velocity is detected based on the five skin areas.

DETAILED DESCRIPTION

Figure 1:
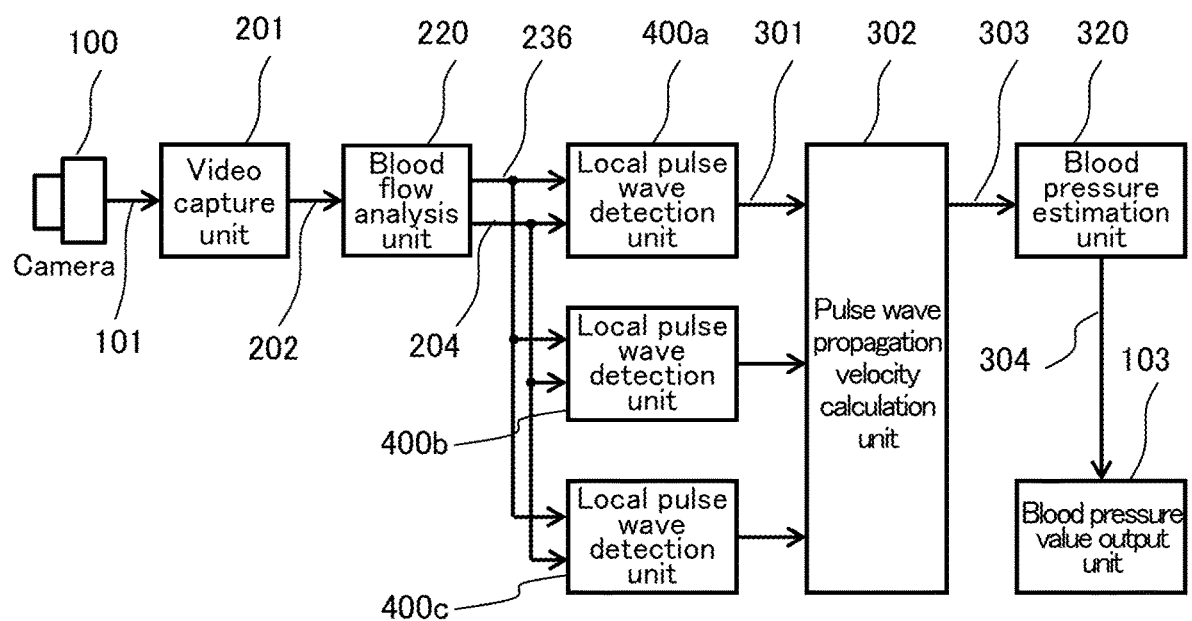
FIG. 1 is a block diagram showing a schematic configuration of a biological information detection device.

Hereinafter, an embodiment of the present invention is described in detail, with reference to the drawings. Note that common components are denoted by the same reference numerals in the drawings and duplicate descriptions thereof are omitted.

FIG. 1 is a block diagram showing a schematic configuration of a biological information detection device of the embodiment. The biological information detection device of the embodiment uses a property that hemoglobin in blood easily absorbs green light, to image reflected light from a living body irradiated with light, analyze blood flow, and calculate a pulse and blood pressure based on a change in the spectral distribution of the reflected light.

The biological information detection device in FIG. 1 includes a camera 100, a video capture unit 201, a blood flow analysis unit 220, and three local pulse wave detection units 400a, 400b, and 400c (hereinafter, collectively referred to as 400), a pulse wave propagation velocity calculation unit 302, a blood pressure estimation unit 320, and a blood pressure value output unit 103.

The video capture unit 201 captures a video signal 101 of the camera 100 as image information on reflected light from a living body at a predetermined frame rate, and converts the image information into video data 202 in an RGB color system, so as to be outputted in chronological order for subsequent analysis. Note that the video capture unit 201 is not limited to capture the video signal 101 of the camera 100 but may be configured to obtain imaging information on reflected light from a living body through a signal cable or a communication network, or may be configured to obtain imaging information on reflected light from a living body from a storage device such as a video recorder.

Note that the biological information detection device analyzes the blood flow based on a change in reflected light between frames of the imaging information obtained from the camera 100, although the details are to be described below.

The blood flow analysis unit 220 analyzes the inputted video data 202 frame by frame, extracts a plurality of image areas (hereinafter referred to as skin areas) including a blood flow image, and outputs, frame by frame, blood flow information 204 including information on reflected light from blood and skin area indication information 236 for obtaining the blood flow image.

The local pulse wave detection units 400a, 400b, and 400c are provided for each skin area including the blood flow image, and detects a pulse wave of the blood flow (blood vessel) from a chronological change in reflected light values of the blood flow, based on the reflected light value of the blood flow in blood flow information 204 analyzed by the blood flow analysis unit 220 and inputted for each frame, and then outputs the fluctuation of the detected pulse wave added to the blood flow information 204, as pulse information 301. Specifically, a change in the volume of a blood vessel caused by a change in blood flow associated with the pulsation of the heart is detected as a change in the spectral distribution of reflected light from the blood flow, to use a chronological change in the spectral distribution as a pulse wave.

The pulse wave propagation velocity calculation unit 302 calculates a pulse wave propagation velocity (PWV or pulse wave velocity in short) 303, based on pieces of the pulse information 301 detected by the local pulse wave detection units 400a, 400b, 400c. Specifically, a difference in distance from the heart between the areas, where the pulse waves are detected, is divided by a difference in phase between the pulse waves.

The blood pressure estimation unit 320 estimates blood pressure information 304 from the pulse wave propagation velocity 303, based on the blood vessel model of Moens-Korteweg and the relationship between elasticity of a blood vessel wall and the blood pressure. The blood pressure value output unit 103 is an output unit to output the blood pressure information 304 estimated by the blood pressure estimation unit 320 to a display device or a terminal.

The functions of the units constituting the above-described biological information detection device can be implemented by hardware circuits using specialized integrated circuits (such as an FPGA or Field Programmable Logic Array), except for the camera 100. Alternatively, the functions can be implemented by a computer including a processor, a storage device (such as a semiconductor memory and a hard disk device), and an input/output device (such as a communication device, a keyboard, a mouse, and a display device). In this case, the functions of the units constituting the biological information detection device are achieved by the processor executing one or more programs stored in the storage device.

Specifically, the computer as a biological information detection device uses the input/output device to input the video data 202, uses the processor to execute the one or more programs to implement the functions as the blood flow analysis unit 220, the local pulse wave detection unit 400, the pulse wave propagation velocity calculation unit 302, and the blood pressure estimation unit 320, and uses the input/output device to output the blood pressure.

Figure 2:
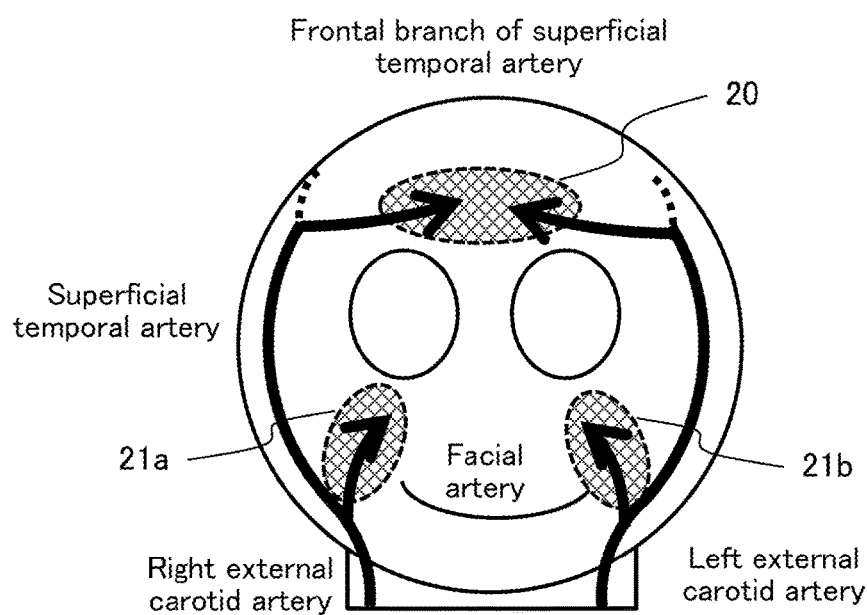
FIG. 2 is a diagram illustrating a blood flow in a face imaged by a camera.

Next, a functional overview of the biological information detection device according to the embodiment is described with reference to FIGS. 2 to 4. FIG. 2 is a diagram illustrating a blood flow in the face captured by the camera 100.

In the head of a living body, blood is known to flow from the heart to the face and scalp through the "left external carotid artery" branched from the "left common carotid artery" and the "right external carotid artery" branched from the "right common carotid artery." As shown in FIG. 2, blood is supplied to a right buccal surface 21a of the face via a "facial artery" branched from the "right external carotid artery", and blood is supplied to a left buccal surface 21b of the face via a "facial artery" branched from the "left external carotid artery." In addition, blood is supplied to a forehead surface 20 via the "frontal branch of the superficial temporal artery." The "frontal branch of the superficial temporal artery" is a branch of the "superficial temporal artery" which is one of the terminal branches of the "right external carotid artery" and the "left external carotid artery."

The forehead surface 20 is located at a position farther from the heart than the right buccal surface 21a and the left buccal surface 21b, and blood is supplied via a different blood vessel, as described above, and thus the pulse waves at the right buccal surface 21a and left buccal surface 21b have different phases from the pulse wave at the forehead 20. In particular, the pulse wave at the forehead surface 20 lags in phase than the pulse waves at the right buccal surface 21a and the left buccal surface 21b.

Specifically, as the path from the heart to the "right common carotid artery" is different from that to the "left common carotid artery," there is also a phase difference between the pulse wave at the right buccal surface 21a and the pulse wave at the left buccal surface 21b. When the phase difference is equal to or less than a predetermined value, it is determined that normal pulse waves have been detected at the right buccal surface 21a and the left buccal surface 21b.

The biological information detection device of the present embodiment detects three blood flows at the skin areas on the forehead 20, the right buccal surface 21a, and the left buccal surface 21b, but when the pulse wave propagation velocity is calculated from the pulse information (pulse wave information) to estimate the blood pressure, the blood pressure can be estimated with two pieces of pulse information. That is, the blood pressure can be estimated with the pulse information at the forehead surface 20 and the pulse information at the right buccal surface 21a or the left buccal surface 21b.

Then, the biological information detection device of the present embodiment either estimates the blood pressure from the pulse information at the forehead surface 20 and the right buccal surface 21a, or estimates the blood pressure from the pulse information at the forehead surface 20 and the left buccal surface 21b. This allows for increasing the latitude in a direction of capturing the face and reducing the restriction on the orientation of the face, to improve the convenience and accuracy of the biological information detection device. The pulse information is selected based on the validity of the pulse information at the right buccal surface 21a and the pulse information at the left buccal surface 21b. When both the pulse information at the right buccal surface 21a and the pulse information at the left buccal surface 21b are valid, they are averaged.

Blood is also supplied to the face via arteries other than the "facial artery" and "superficial temporal artery." For this reason, the distance from the heart differs depending on the area, over the entire face, and there is a phase difference in the pulse wave (pulse) between the areas. The biological information detection device of the present embodiment detects the pulse wave at the skin areas of the forehead surface 20, the right buccal surface 21a, and the left buccal surface 21b, but the present invention is not limited to these areas.

The biological information detection device detects blood flow at the at least three skin areas between which there is one or more phase differences in the blood flow. Specifically, the blood flow are detected at such skin areas that one skin area is located on the center line of the face, and the other skin areas are located bilaterally symmetric to the center line of the face and have the blood flow paths closer to the heart than the skin area located on the center line. This allows for increasing the latitude in a direction of capturing the face and reducing the restriction on the orientation of the face, to improve the convenience and accuracy of the biological information detection device.

Figure 3A:
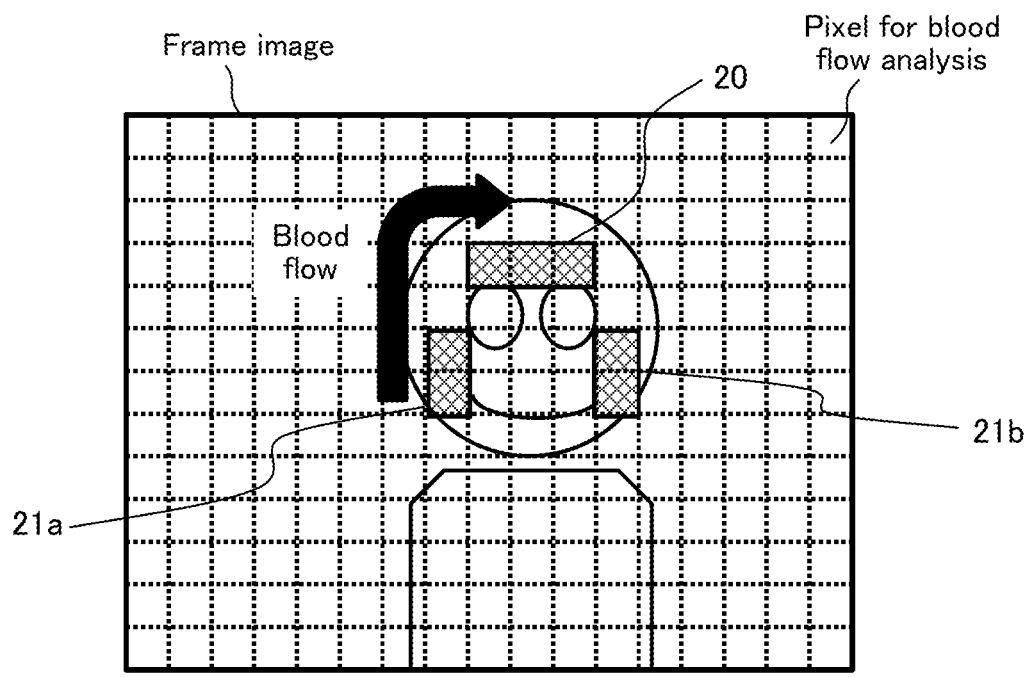
FIG. 3A shows a frame image including skin areas for obtaining blood flow information, from which a pulse wave is detected, at a forehead surface, a right buccal surface, and a left buccal surface in imaging information on reflected light.

Next, a description is given of dividing the areas at the forehead surface 20, the right buccal surface 21a, and the left buccal surface 21b, at which pulse waves (pulses) are detected, and detecting a phase difference between the pulse waves. FIG. 3A shows a frame image including skin areas for obtaining blood flow images, from which pulse waves are detected, at the forehead surface 20, the right buccal surface 21a, and the left buccal surface 21b in imaging information on reflected light from a living body captured by the camera 100. The imaging information is such information that frame images, each having pixels arrayed two-dimensionally, are sequenced chronologically.

The biological information detection device analyzes pixels for blood flow analysis, for each frame image of the imaging information, and extracts pixels corresponding to the skin areas at the forehead surface 20, the right buccal surface 21a, and the left buccal surface 21b. Then, the spectral distribution values of the reflected light from the blood flow, indicated by the extracted pixels, are added or averaged for each skin area, to obtain the blood flow information 204. The biological information detection device chronologically sequences the pieces of the blood flow information 204 at the skin areas, to obtain pulse wave information 207.

Figure 3B:
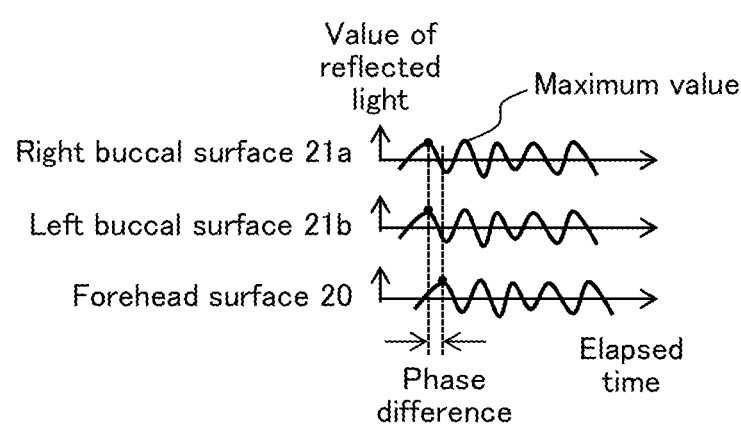
FIG. 3B shows an example of pulse wave information.

FIG. 3B shows an example of the pulse information 301 (pulse wave information 207). In the skin area of a living body, the amount of hemoglobin at the skin area increases or decreases with a change in the volume of blood vessels due to a change in blood flow, so that there is a change in the spectral distribution value of the reflected light. Then, when values of the reflected light in the blood flow information 204 are sequenced chronologically, pulse waveforms (pulse information) corresponding to the heartbeat cycle are obtained for each of the right buccal surface 21a, the left buccal surface 21b, and the forehead surface 20, as shown in FIG. 3B.

Note that the biological information detection device obtains a pulse wave from a temporal change in a spectral distribution value (hue) of reflected light, to detect a phase difference between the skin areas, as will be described below in detail. Pulse waves caused by a temporal change in value of the reflected light is shown for the purpose of illustration, as in FIG. 3B, but the phase difference between the skin areas is the same in each case (the same applies to the subsequent drawings).

The phase difference between the pulse waves at the right buccal surface 21a, the left buccal surface 21b, and the forehead surface 20 is obtained by calculating a time difference between the maximum or minimum values of the respective pulse waveforms, as shown in FIG. 3B. The pulse wave at the forehead surface 20 has a waveform lagging in phase than the pulse wave at the right buccal surface 21a or the left buccal surface 21b, as described above, and then the pulse wave propagation velocity is calculated from the obtained phase difference to estimate the blood pressure.

The biological information detection device sets or determines the skin area for detecting the pulse wave as follows, to obtain the blood flow information 204, although the details will be described below. One way is to register the colors of the forehead surface 20, the right buccal surface 21a, and the left buccal surface 21b for detecting pulse waves on the face of a living body (subject), as colors for determining the skin area, and then to refer thereto when the blood flow information 204 is obtained. Specifically, a color range for determining the skin area is defined as the color information in the imaging information, and when the pixel of the frame image has the color determined as such, the blood flow information 204 is obtained as the pixel of the skin area.

In addition, the area coordinates (pixel position information) of the skin areas of the forehead surface 20, the right buccal surface 21a, and the left buccal surface 21b are registered, to extract pixels from the frame image based on the area coordinates of the skin areas, that is, to obtain the blood flow information 204 as the pixels of the skin areas.

Figure 4:
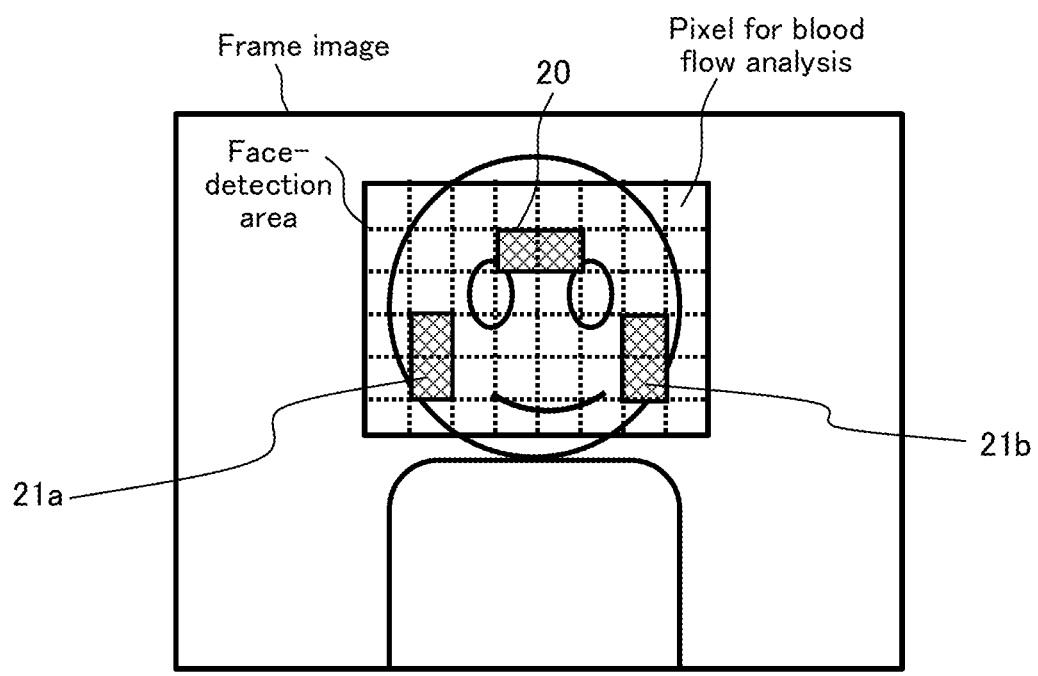
FIG. 4 is a diagram illustrating a case of extracting a face detection area from a frame image to obtain blood flow information.

Incidentally, the skin areas of the forehead surface 20, the right buccal 21a, and the left buccal surface 21b belong to the face, as shown in FIG. 4, and thus the face may be extracted from the frame image using the Viola-Jones algorithm or the like to obtain the blood flow information 204 on the face-detected image area (face-detection area), as illustrated in FIGS. 3A and 3B. This reduces a burden of obtaining the blood flow information 204.

Figure 5:
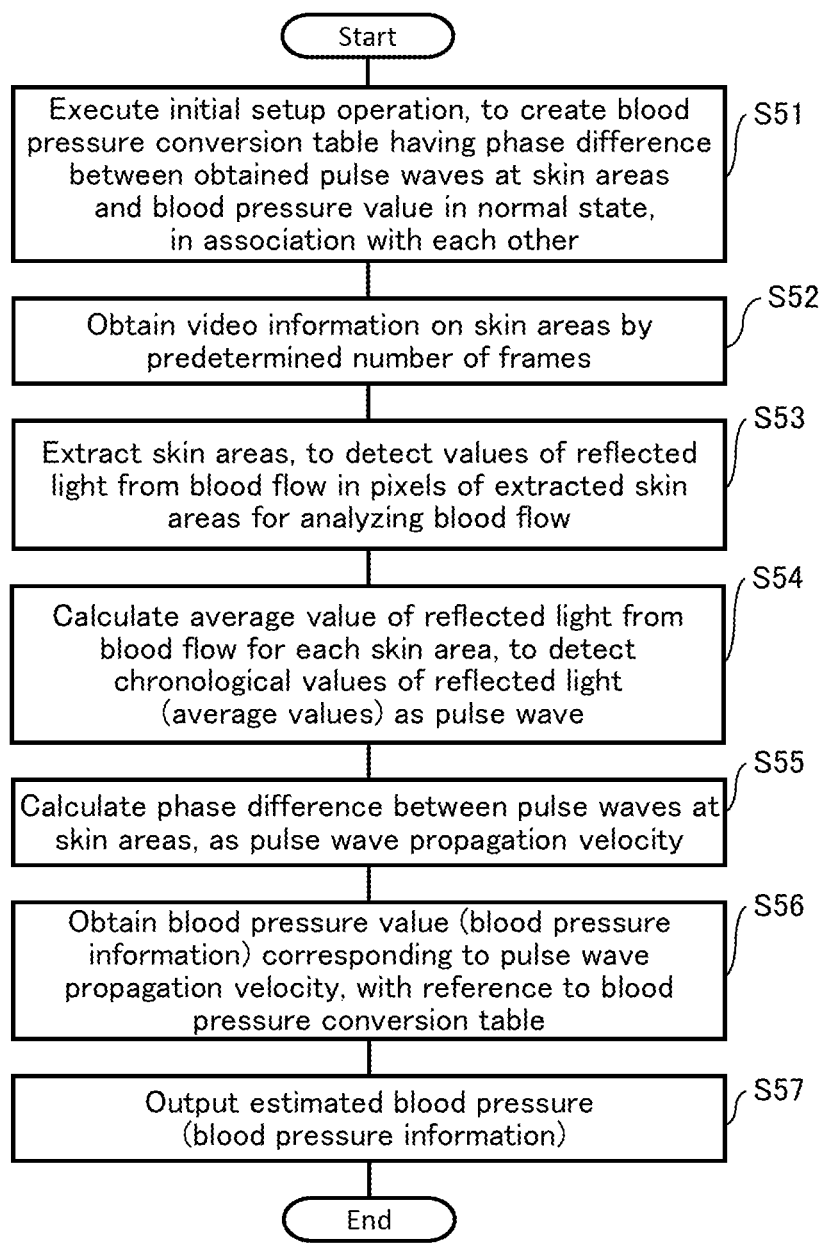
FIG. 5 is a flowchart of processing by the biological information detection device.

Next, a description is given of a general flow of processing by the biological information detection device, with reference to FIG. 5. Note that when the blood pressure is estimated in the processing flow in FIG. 5, such a technique is used to estimate the blood pressure that a correspondence table between a phase difference in pulse waves and the blood pressure value (a blood pressure conversion table 326) is referred to, as an alternative to a technique of estimating the blood pressure information 304 from the pulse wave propagation velocity 303 based on the blood vessel model of Moens-Korteweg and the relationship between elasticity of the blood vessel wall and the blood pressure.

In step S51, the biological information detection device executes initial setup operation to detect pulse flow information of a living body (subject) in a normal state, for each skin area, calculate a phase difference between pulse waves (pulses), and register the result into the blood pressure conversion table 326, as well as to register the real blood pressure value measured by a hemomanometer at this time into the blood pressure conversion table 326 in association with the phase difference, to create the blood pressure conversion table 326. Note that sets of the phase difference in pulse waves and the blood pressure value under different conditions are desirably registered in the blood pressure conversion table 326.

In step S52, the video capture unit 201 of the biological information detection device obtains video information on reflected light from the face or the like of the living body, for each frame, by a predetermined number of frames.

In step S53, the blood flow analysis unit 220 of the biological information detection device executes processing of blood flow analysis to extract the face of the living body (subject) for each frame of the obtained video information, and then extract skin areas of the forehead surface 20, the right buccal surface 21a and the left buccal surface 21b from the extracted screen image to detect values of the pixels of the skin areas as the values of the reflected light from the blood flow for analyzing the blood flow.

In step S54, the local pulse wave detection unit 400 (400a, 400b, 400c) of the biological information detection device calculates an average value of the reflected light from the blood flow in the skin area, for each of the skin areas extracted in step S53. Then, the local pulse wave detection unit 400 of the biological information detection device detects average values of reflected light from the blood flow between (chronologically sequenced) frames, as pulse wave information at each skin area.

In step S55, the pulse wave propagation velocity calculation unit 302 evaluates the validity of the pulse wave information in the skin areas of the right buccal surface 21a and the left buccal surface 21b detected in step S54, and calculates a phase difference between the pulse waves at the skin areas of the forehead surface 20 and the right buccal surface 21a, a phase difference between the pulse waves at the skin areas of the forehead surface 20 and the left buccal surface 21b, or an average of said two phase differences, as a value of the pulse wave propagation velocity.

In step S56, the blood pressure estimation unit 320 of the biological information detection device obtains a blood pressure value corresponding to the pulse wave propagation velocity (phase difference) obtained in step S55, with reference to the blood pressure conversion table 326 registered in step S51, as estimated blood pressure (blood pressure information).

In step S57, the blood pressure value output unit 103 outputs the blood pressure information obtained in step S56 to a display device or a terminal.

Figure 6:
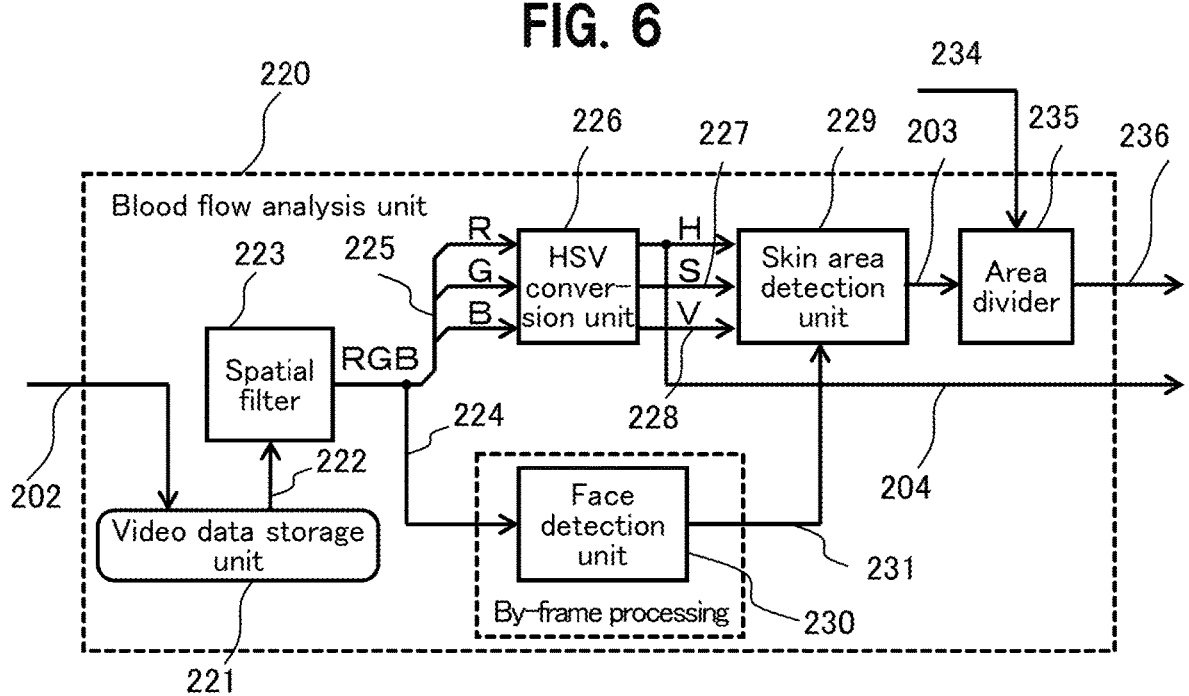
FIG. 6 is a block diagram showing a configuration of a blood flow analysis unit.

Hereinbelow, a description is given in detail of the blocks in the biological information detection device in FIG. 1. FIG. 6 is a block diagram showing a configuration of the blood flow analysis unit 220. The blood flow analysis unit 220 includes a video data storage unit 221, a spatial filter 223, an HSV conversion unit 226, a skin area detection unit 229, a face detection unit 230, and an area divider 235, and executes video processing for each pixel of the video data 202.

The video data storage unit 221 inputs the video data 202 (in an RGB color system) outputted from the video capture unit 201 (see FIG. 1) and outputs delayed video data 222, which is added with video data having a line delay by taps of the convolution kernel, to the spatial filter 223.

The spatial filter 223 inputs the delayed video data 222, smoothes the delayed video data 222 of the pixel of interest and surrounding pixels, such as by weighted averaging, and outputs smoothed video data 224.

More specifically, the spatial filter 223 is a filter to apply a convolution kernel of 3 taps in the vertical and horizontal directions, or 3-by-3 pixels, (determinant) in smoothing pixels, for example. In this case, convolution operation is executed on 3-by-3 pixels centered around the pixel of interest, using the convolution kernel, to obtain a value as the smoothed video data 224 of the pixel of interest. Note that elements of the determinant of the convolution kernel are coefficients for weighted averaging, for example, and can be appropriately determined using an average value distribution, a Gaussian distribution, or the like, as long as the sum of the elements becomes 1.0.

The HSV conversion unit 226 inputs unpacked information 225 having the smoothed video data 224 decomposed into R (red), G (green), and B (blue), and converts the unpacked information 225 into video data in a color system of the HSV color space composed of the hue information 204 (H), saturation information 227 (S), and value information 228 (V).

The biological information detection device treats a change in a blood flow as a change in amount of blood hemoglobin per area, and detects a change in a spectral distribution of reflected light due to G light absorption of hemoglobin. In order to easily execute this detection, the HSV conversion unit 226 converts video data in the RGB color system into video data in the HSV color system to detect a blood flow. This causes the hue information 204 (H) to be outputted as the blood flow information 204, which is output information of the blood flow analysis unit 220.

The face detection unit 230 inputs the smoothed video data 224, executes face detection for each frame using the Viola-Jones algorithm, for example, and outputs face area information 231, indicating position information on a face area including a skin area for blood flow detection, to the skin area detection unit 229. Providing the face detection unit 230 allows for detecting a blood flow simultaneously or selectively for a plurality of living bodies (subjects), although not described in detail.

The skin area detection unit 229 inputs the hue information 204 (H), the saturation information 227 (S), the value information 228 (V), and the face area information 231, and outputs skin area indication information 203 indicating that a blood flow image is included.

Here, the skin area detection unit 229 is described in detail. The skin area detection unit 229 executes either one of a technique of specifying a range in the color space of the skin area (partial color space) and outputting the skin area indication information 203 when the color space of the pixel of the video data, having the video data 202 converted into video data in the HSV color system, falls within the specified range (first skin area detection technique), and a technique of specifying an area position of the skin area and outputting the skin area indication information 203 when the pixel of the video data, having the video data 202 converted into video data in the HSV color system, falls within the range of the specified area position (second skin area detection technique).

Figure 7:
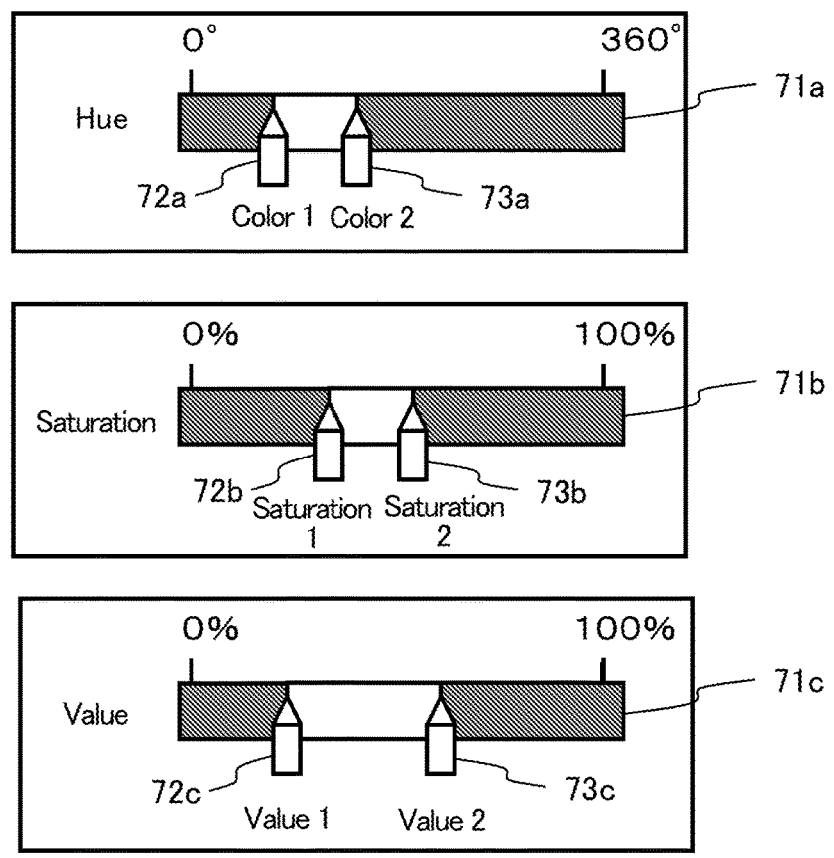
FIG. 7 shows an example of a screen for specifying ranges in a color space (partial color space) of the skin area.

First, the first skin area detection technique is described with reference to FIG. 7. FIG. 7 shows an example of a screen for specifying color ranges in the color space (partial color space) of the skin area displayed on a predetermined display device.

The specification screen includes slide bars 71a, 71b, and 71c (hereinafter, collectively referred to as 71) indicating the entire range of the hue H, the saturation S, and the value V, respectively, and two cursors 72 (72a, 72b, 72c) and 73 (73a, 73b, 73c) slidable along the slide bar 71. This allows the user to slide the cursors 72 and 73 as required, using an input device (not shown) such as a mouse, to freely set the color space range of the skin area.

In FIG. 7, the slide bar 71a in the range of 0 to 360 degrees is displayed for the hue H, for example. Here, 0 degrees (360 degrees) indicate red, 120 degrees indicate green, and 240 degrees indicate blue, and the hue H for the color space range of the skin area (partial color space) is specified to be a color between Color 1 and Color 2. Similarly, for the saturation S, 0% indicates a light color while 100% indicates a dark color, and the saturation S of the partial color space is specified by Saturation 1 and Saturation 2. For the value V, 0% indicates dark while 100% indicates light, and the value V of the partial color space is specified by Value 1 and Value 2.

Note that the range of the partial color space is specified for all of the hue H, the saturation S, and the value V in the example in FIG. 7, but it is sufficient that the range is specified for at least the hue H. In particular, the specification of the range for the saturation S may be omitted.

In this manner, the skin area detection unit 229 (see FIG. 6) suitably sets whether or not a pixel in the video data 202 belongs to the skin area for pulse flow detection, based on the skin color of the individual and lighting conditions. On determining that the pixel belongs to the skin area, the skin area detection unit 229 outputs "1" in the skin area indication information 203.

Figure 8A:
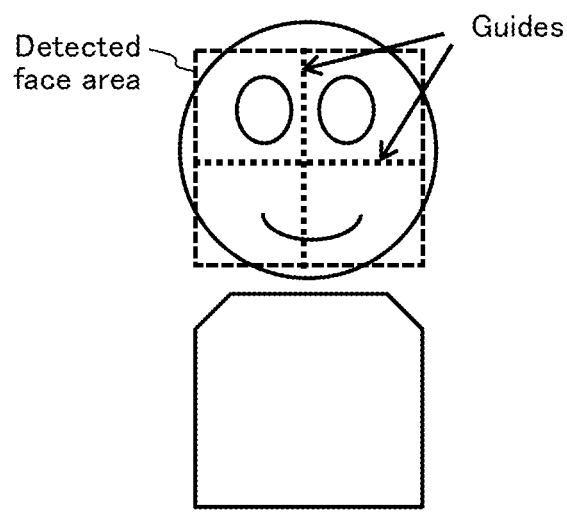
FIG. 8A is a diagram to show a technique of specifying area positions of skin areas, using center lines of the face detected by a face detector, as guides.
Figure 8B:
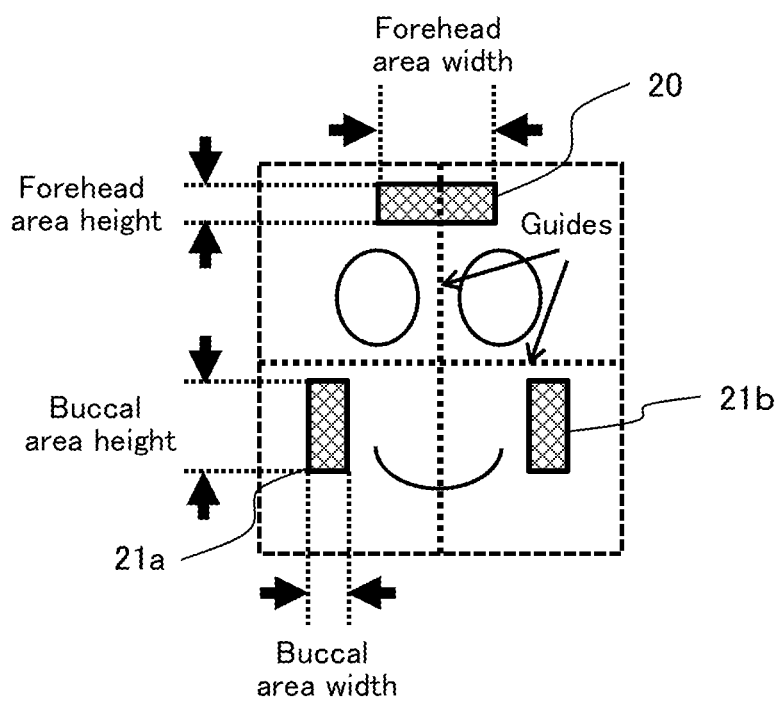
FIG. 8B is another diagram to show the technique of specifying area positions of skin areas, using the center lines of the face detected by the face detector, as the guides.
Figure 9A:
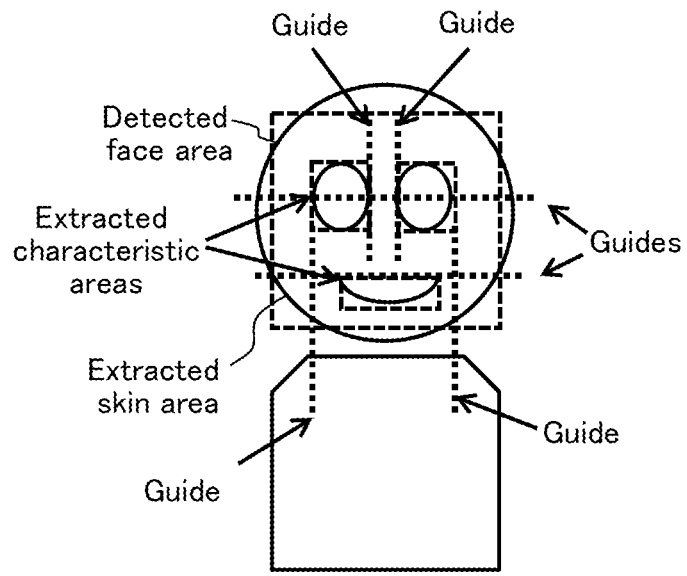
FIG. 9A is a diagram to show a technique of specifying area positions of skin areas, using characteristic portions (eyes, mouth) of the face detected by the face detection unit, as guides.
Figure 9B:
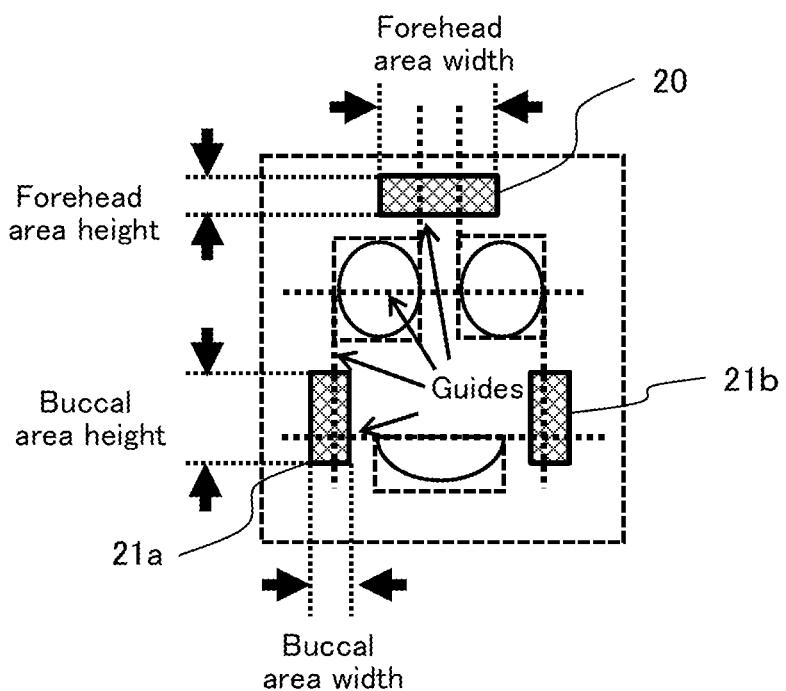
FIG. 9B is another diagram to show the technique of specifying area positions of skin areas, using the characteristic portions (eyes, mouth) of the face detected by the face detection unit, as the guides.

Next, the second skin area detection technique is described. FIGS. 8A and 8B show a technique of specifying area positions of the skin areas, using center lines of the face detected by the face detection unit 230, as guides. FIGS. 9A and 9B show a technique of specifying area positions of skin areas, using characteristic portions (eyes, mouth) of the face detected by the face detection unit 230, as guides.

First, a description is given of the technique of specifying the area positions of the skin areas in FIGS. 8A and 8B. FIG. 8A is a diagram to show a face area of a living body (area enclosed by a broken-line frame) detected by the face detection unit 230 from the video data 202 (smoothed video data 224). The face detection unit 230 obtains guides of two axes connecting the midpoints of the frame lines of the extracted face area frame.

Then, the face detection unit 230 obtains area coordinates (pixel position information) of the skin areas of the forehead surface 20, the right buccal surface 21a, and the left buccal surface 21b in the frame image with reference to the guides, based on the preset area information (relative position from the guide, the area width, and the area height) on the skin areas of the forehead surface 20, the right buccal surface 21a, and the left buccal surface 21b, as shown in FIG. 8B, and then gives the results as the face area information 231 to the skin area detection unit 229.

The skin area detection unit 229 determines whether or not the pixel in the video data 202 belongs to the skin area for pulse wave detection, based on the face area information 231, and, if the pixel is determined to belong to the skin area, outputs "1" in the skin area indication information 203.

Next, a description is given of a technique of specifying the area positions of the skin areas, as shown in FIGS. 9A and 9B. The face detection unit 230 detects the face area of a living body (area enclosed by a broken-line frame) from the video data 202 (smoothed video data 224), and then extracts the eyes and the mouth from the face area, as shown in FIG. 9A. Then, the face detection unit 230 obtains guides as positional references for the skin areas of the forehead surface 20, the right buccal surface 21a, and the left buccal surface 21b, from area frames enclosing the extracted eyes and mouth. For example, a center line and/or side of the area frame enclosing the extracted eye or mouth is/are used as the guide(s). Note that the facial characteristics may include a nose, eyebrows, and ears.

The face detection unit 230 then obtains area coordinates (pixel position information) of the skin areas of the forehead surface 20, the right buccal surface 21a, and the left buccal surface 21b in the frame image, with reference to the guides, based on the preset area information (the relative position from the guide, the area width, and the area height) on the skin areas of the forehead surface 20, the right buccal surface 21a, and the left buccal surface 21b, as shown in FIG. 9B, and gives the results as the face area information 231 to the skin area detection unit 229.

The skin area detection unit 229 determines whether or not the pixel in the video data 202 (the video data converted into video data in the HSV color space) belongs to a skin area for pulse wave detection, based on the face area information 231, and, in a case of determining that the pixel belongs to the skin area, outputs "1" in the skin area indication information 203.

Returning to FIG. 6, the area divider 235 is described. The region divider 235 inputs the skin area indication information 203, indicating that the blood flow image detected by the skin area detecting unit 229 is included, and area count parameter 234, indicating the number of skin areas, and outputs the skin area indication information 203 (skin area indication information 236) for each skin area to the local pulse wave detection unit 400 to be described below.

Hereinabove, such a configuration has been described that the HSV conversion unit 226 converts the video data 202 into video data in the HSV color system, and then the skin area detection unit 229 detects the skin area. However, the video data in the RGB color system may be converted to video data in the HSL (Hue, Saturation, Lightness) color system. In this case, the blood flow is detected based on the hue information, to allow for executing detection resistant to environmental changes. Note that the lightness information indicates brightness, that is, intensity.

Figure 10:
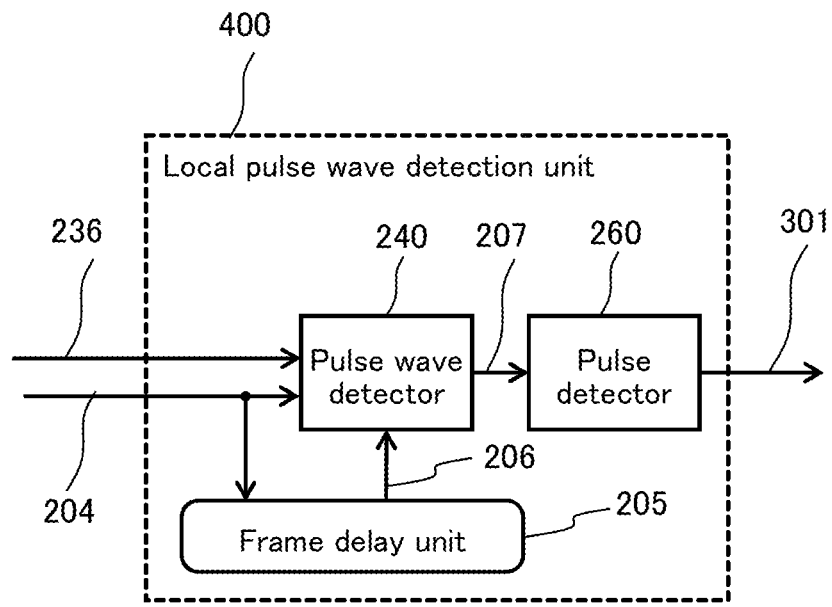
FIG. 10 is a block diagram of a local pulse wave detection unit.

Next, a description is given in detail of the local pulse wave detection unit 400 (400a, 400b, 400c) in the biological information detection device in FIG. 1. FIG. 10 is a diagram to show one of the local pulse wave detection units 400a, 400b, and 400c, which are provided to correspond to the respective skin areas of the forehead surface 20, the right buccal surface 21a, and the left buccal surface 21b.

The local pulse wave detection unit 400 includes a pulse wave detector 240 to detect a pulse wave of the blood flow from the blood flow information 204 (hue information 204), a frame delay unit 205 to temporally delay the blood flow information 204 (hue information 204), and a pulse detector 260 to detect a pulse from the pulse wave information 207 detected by the pulse wave detector 240, and outputs the pulse information 301 obtained by adding pulse information to the pulse wave information 207. The pulse information 301 detected by each of the local pulse wave detection units 400a, 400b, and 400c is given to the pulse wave propagation velocity calculation unit 302.

Figure 11:
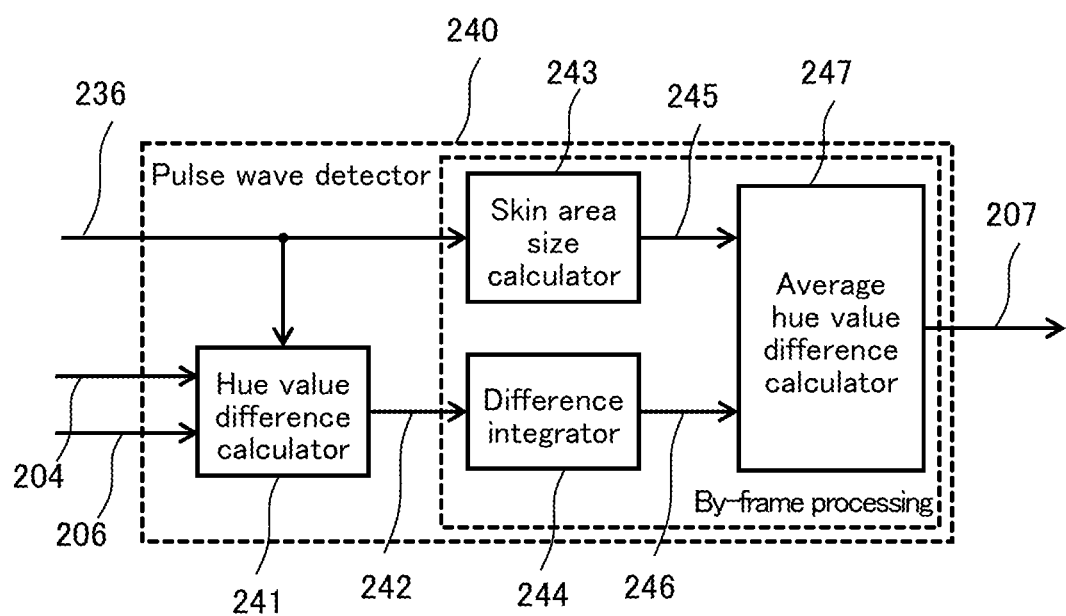
FIG. 11 is a diagram to show details of a pulse wave detector in the local pulse wave detection unit.

FIG. 11 is a diagram to show details of the pulse wave detector 240 in the local pulse wave detection unit 400 in FIG. 10. The pulse wave detector 240 includes a hue value difference calculator 241, a skin area size calculator 243, a difference integrator 244, and an average hue value difference calculator 247, as shown in FIG.

The hue value difference calculator 241 inputs the skin area indication information 236, the blood flow information 204 (hue information 204), and delayed hue information 206 obtained by frame-delaying the hue information 204 by the frame delay unit 205 (see FIG. 10), and outputs hue difference information 242, which is set, as follows, depending on the value of "1" or "0" in the skin area indication information 236.

The hue value difference calculator 241 outputs the hue difference information 242, which is a difference between the inputted hue information 204 and the delayed hue information 206 (i.e., a difference between the hue information 204 on the current frame and the hue information 204 on a frame preceding the current frame), when a signal of a pixel in the skin area is inputted (that is, when "1" is inputted as the skin area indication information 236), while outputs "0" as a value of the hue difference information 242, when a signal of a pixel outside the skin area is inputted (i.e., when "0" is inputted as the skin area indication information 236).

The skin area size calculator 243 inputs the skin area indication information 236 indicating that the pixel belongs to the skin area, and counts the number of pixels in the skin area (the area where the skin area indication information 236 has "1") for the frame to be processed, and outputs the count value as skin area size information 245.

The difference integrator 244 inputs the hue difference information 242, integrates the values of pieces of the hue difference information 242 on the pixels in the skin area, and outputs the integrated value as integrated hue difference information 246.

The average hue value difference calculator 247 inputs the skin area size information 245 and the integrated hue difference information 246, and outputs a value obtained by dividing the value of the integrated hue difference information 246 by the value of the skin area size information 245, as the pulse wave information 207. The pulse wave information 207 is an average value of pieces of the hue difference information 242 on the pixels belonging to the skin area in the frame, that is, variation in a value of the average hue information 204 in the skin area of a living body (subject).

Figure 12:
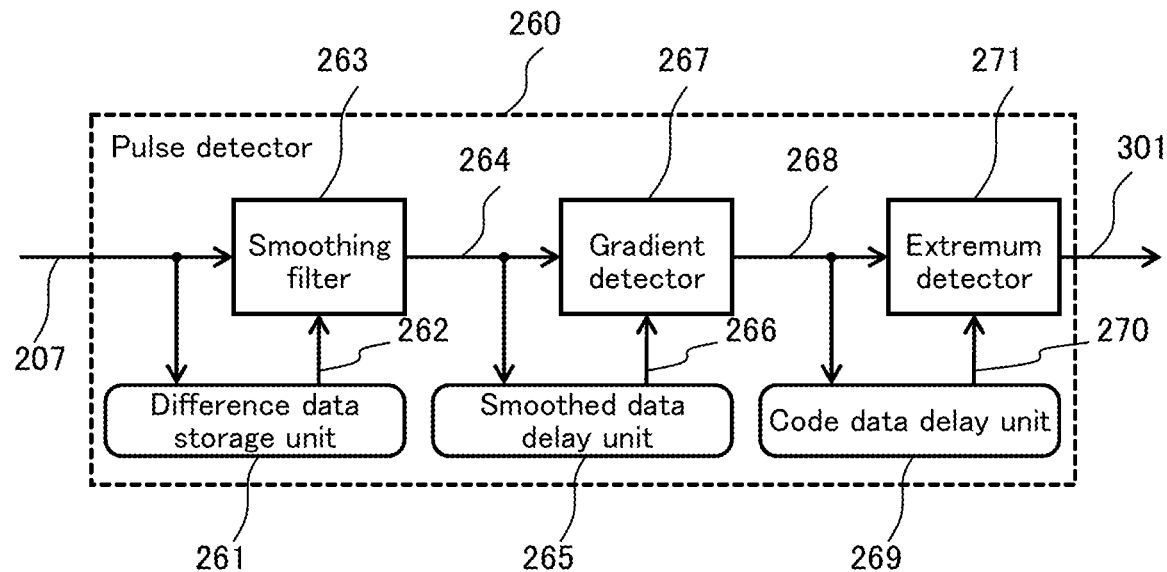
FIG. 12 is a block diagram to show details of an example configuration of a pulse detector.

FIG. 12 is a block diagram to show details of an example configuration of the pulse detector 260. The pulse detector 260 includes a difference data storage unit 261, a smoothing filter 263, a smoothed data delay unit 265, a gradient detector 267, a code data delay unit 269, and an extremum detector 271, as shown in FIG. 12. The pulse detector 260 generates the pulse information 301 from the pulse wave information 207 outputted from the pulse wave detector 240 for each frame, that is, outputted from the pulse wave detector 240 over time.

The difference data storage unit 261 inputs and temporarily stores the pulse wave information 207, and outputs pieces of delayed pulse wave information 262, which are pieces of the pulse wave information 207 on several frames preceding the current frame. The smoothing filter 263 inputs the pulse wave information 207 and pieces of the delayed pulse wave information 262 on several frames, smoothes them, that is, smoothes pieces of the pulse wave information 207 on frames, and outputs pieces of smoothed pulse wave information 264.

The smoothed data delay unit 265 inputs the smoothed pulse wave information 264, stores values for the frames, and outputs pieces of delayed smoothed pulse wave information 266. The delayed smoothed pulse wave information 266 corresponds to the smoothed pulse wave information 264 obtained for a frame temporally preceding the frame currently in process.

The gradient detector 267 obtains a temporal variation (that is, a gradient) of the smoothed pulse wave information 264 with respect to the delayed smoothed pulse wave information 266 (that is, the smoothed pulse wave information 264 obtained for a frame preceding the current frame). Then, the gradient detector 267 outputs the sign of the gradient as gradient information 268.

Specifically, the gradient detector 267 may obtain the gradient between pieces of the smoothed pulse wave information 264 on two consecutive frames, or may obtain the gradient between pieces of the smoothed pulse wave information 264, each obtained by averagely smoothing a plurality of consecutive frames. In the latter case, the gradient detector 267 may calculate the gradient from the average of pieces of the smoothed pulse wave information 264 on current consecutive frames, and the average of pieces of the smoothed pulse wave information 264 on another consecutive frames preceding the current consecutive frames, for example.

The code data delay unit 269 inputs the gradient information 268, stores the values of the gradient information 268 on frames, and outputs delayed gradient information 270. The delayed gradient information 270 corresponds to the gradient information 268 obtained for frames temporally preceding the frames currently in process.

The extremum detector 271 inputs the gradient information 268 and the delayed gradient information 270, and obtains a frame having the sign of the gradient changed from a positive value to a negative value or a frame having the sign of the gradient changed from a negative value to a positive value. This means that the smoothed pulse wave information 264 has changed from increasing to decreasing or has changed from decreasing to increasing, that is, has reached a maximum value or a minimum value, at the time corresponding to the frame obtained in this manner.

The extremum detector 271 thus inputs the gradient information 268 and the delayed gradient information 270, adds "1" to the pulse wave information 207, as extremum information, for a frame having the sign of the gradient changed from a positive value to a negative value, and outputs the result as the pulse information 301. Alternatively, the extremum value detector 271 adds "−1" to the pulse wave information 207, as extremum information, for a frame having the sign of the gradient changed from a negative value to a positive value, while adds "0" to the pulse wave information 207 for a frame having the sign of the gradient not changed.

As described above, in the present embodiment, the smoothing filter 263 temporally smoothes the pulse wave information 207, to prevent a pulse wave from being erroneously detected due to minute fluctuation of the pulse wave information 207 caused by noise or the like. In addition, in the present embodiment, the gradient detector 267 detects the variation (gradient) of the smoothed pulse wave information 264 between adjacent frames, and based on the result, the extremum detector 271 detects the maximum value or the minimum value of the smoothed pulse wave information 264. The maximum value or the minimum value detected in this manner are used when the heart rate is counted, for example.

The extremum information detected by the extremum detector 271 is added to the pulse wave information 207, and outputted as the pulse information 301. The pulse information 301 having the extremum information added, as an output from the pulse detector 260, is given to the pulse wave propagation velocity calculation unit 302, as the pulse information 301 from the local pulse wave detection unit 400 for each skin area. The pulse wave propagation velocity calculation unit 302 obtains the pulse information 301 from each of the local pulse wave detection unit 400a for the forehead surface 20, the local pulse wave detection unit 400b for the right buccal surface 21a, and the local pulse wave detection unit 400c for the left buccal surface 21b.

As described above, the pulse wave propagation velocity calculation unit 302 obtains a time difference between the time points having the same extremum information (e.g., the maximum value) from the pulse information 301 at the forehead surface 20 and the pulse information 301 at the right buccal surface 21a, as a phase difference between the pulse waves at the forehead surface 20 and the right buccal surface 21a. Then, the pulse wave propagation velocity 303 is calculated from the distance difference between the forehead surface 20 and the right buccal surface 21a, and the phase difference between the pulse waves at the forehead surface 20 and the right buccal surface 21a.

Figure 13:
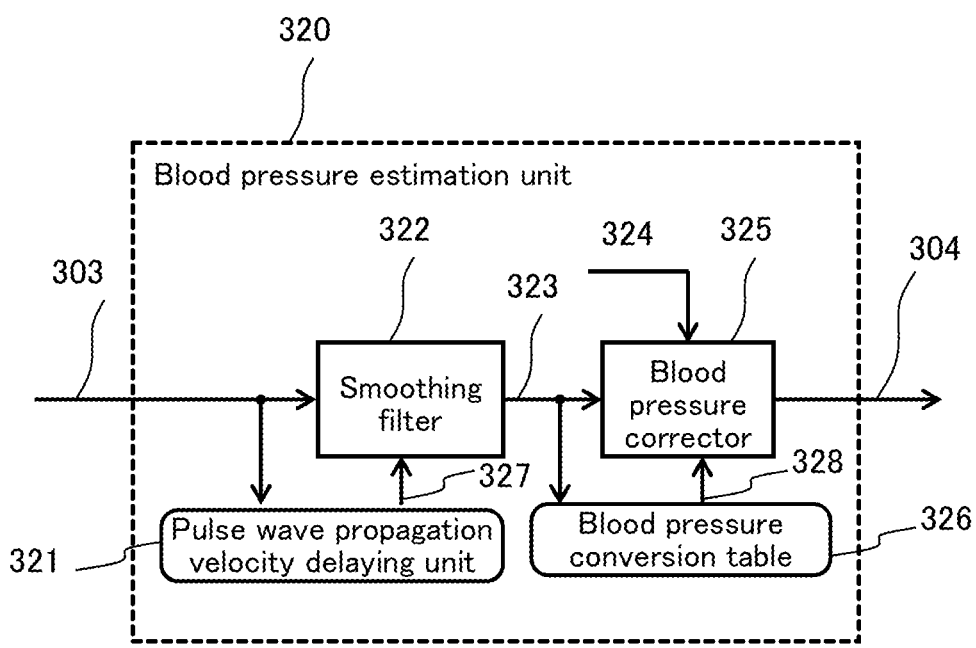
FIG. 13 is a block diagram to show details of an example configuration of a blood pressure estimation unit.

FIG. 13 is a block diagram to show details of an example configuration of the blood pressure estimation unit 320. The blood pressure estimation unit 320 includes a pulse wave propagation velocity delaying unit 321, a smoothing filter 322, a blood pressure conversion table 326, and a blood pressure corrector 325, as shown in FIG. 13.

Here, the pulse wave propagation velocity delaying unit 321 stores the value of the pulse wave propagation velocity 303 inputted over a plurality of frames, and outputs a delayed pulse wave propagation velocity 327. The smoothing filter 322 inputs and averages the pulse wave propagation velocities 303 and delayed pulse wave propagation velocities 327 for a plurality of frames, and outputs a smoothed pulse wave propagation velocity 323.

The blood pressure conversion table 326 inputs the smoothed pulse wave propagation velocity 323, searches the table, and outputs blood pressure conversion information 328 as a source of blood pressure. According to the Maines-Cortebague equation, the blood pressure value (P) in diastole is proportional to the square of the pulse wave velocity (PWV). That is, $P=c*PWV^2$. Note that the proportionality constant "c" depends on various kinds of biological information (such as age, gender, blood vessel radius, and blood density) of the subject. Then, the blood pressure conversion table 326 inputs the value of the smoothed pulse wave propagation velocity 323 as the pulse wave propagation velocity (PWV), and outputs the blood pressure value for predetermined representative biological information as the blood pressure conversion information 328.

The blood pressure corrector 325 inputs the smoothed pulse wave velocity 323, the blood pressure conversion information 328, and a blood pressure correction parameter 324, corrects the blood pressure conversion information 328, and outputs the blood pressure information 304. Here, the blood pressure correction parameter 324 is a numerical value necessary for determining the proportionality constant "c," such as age, gender, blood vessel radius, and blood density. That is, the blood pressure corrector 325 corrects the blood pressure value for the representative biological information obtained by the blood pressure conversion table 326 based on the biological information on the subject.

Note that the blood pressure estimation unit 320 in FIG. 13 estimates the blood pressure value of the subject using the pulse wave propagation velocity 303, the blood pressure conversion table 326, and the blood pressure correction parameter 324, but may calculate the blood pressure information 304 on the subject using a mathematical model based on the Maines-Cortebague equation or the like.

In addition, as illustrated in FIG. 5, the real blood pressure values may be measured for each living body (subject) to detect pulse waves at predetermined skin areas for obtaining a phase difference in the blood flow so that the phase difference in pulse waves is stored in the blood pressure conversion table 326 in association with the measured blood pressure, as an initial setup operation (calibration) of the biological information detection device. In this case, the pulse wave propagation velocity calculation 302 assumes the phase difference obtained from the pulse information 301 at the skin areas, as the pulse wave propagation velocity 303, and stores the phase difference in the blood pressure conversion table 326.

Modifications

Next, a description is given of a configuration of the biological information detection device capable of executing adaptive processing based on brightness of the video to reduce degradation in detection accuracy and erroneous detection, even with a sudden variation in external light when capturing an image of the face of a living body (subject). Specifically, there are differences in the configurations of the blood flow analysis unit 220 (see FIG. 6) of the biological information detection device and the pulse wave detector 240 (see FIG. 11) of the local pulse wave detection unit 400.

Figure 14:
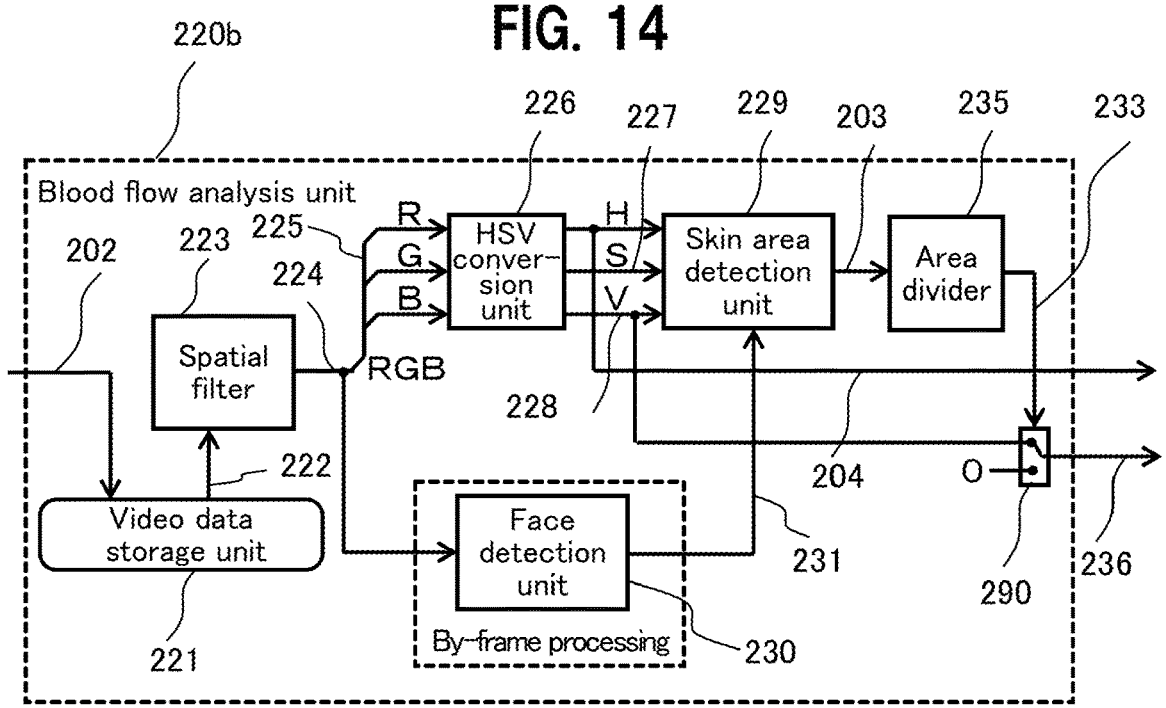
FIG. 14 is a block diagram of a blood flow analysis unit adaptive to variation in external light.

FIG. 14 is a block diagram to show details of an example configuration of a blood flow analysis unit 220*b* adaptive to variation in external light. The blood flow analysis unit 220*b* includes the video data storage unit 221 the spatial filter 223, the HSV conversion unit 226, the skin area detection unit 229, the face detection unit 230, a selector 290, the area divider 235, as shown in FIG. 14.

The blood flow analysis unit 220*b* has such a configuration that the selector 290 is added to the blood flow analysis unit 220 in FIG. 6. The configuration is different from that in FIG. 6 on the point that the skin area indication information 236 is outputted not from the area divider 235 but from the selector 290. The rest of the blood flow analysis unit 220*b* remains the same as that of the blood flow analysis unit 220 in FIG. 6, and thus a description thereof is omitted here.

Specifically, the value information 228 hooked to the selector 290 or a value of "0" is outputted in the skin area indication information 236, based on selection information 233 outputted from the area divider 235. This causes the skin area indication information 236 from the blood flow analysis unit 220*b* to have the value information 228 when an area belongs to the skin area, while to have a value of "0" when an area fails to belong to any skin area, in contrast to the skin area indication information 236 from the blood flow analysis unit 220 in FIG. 6 to have a value of "1" or "0" to indicate whether or not an area belongs to the skin area.

Figure 15:
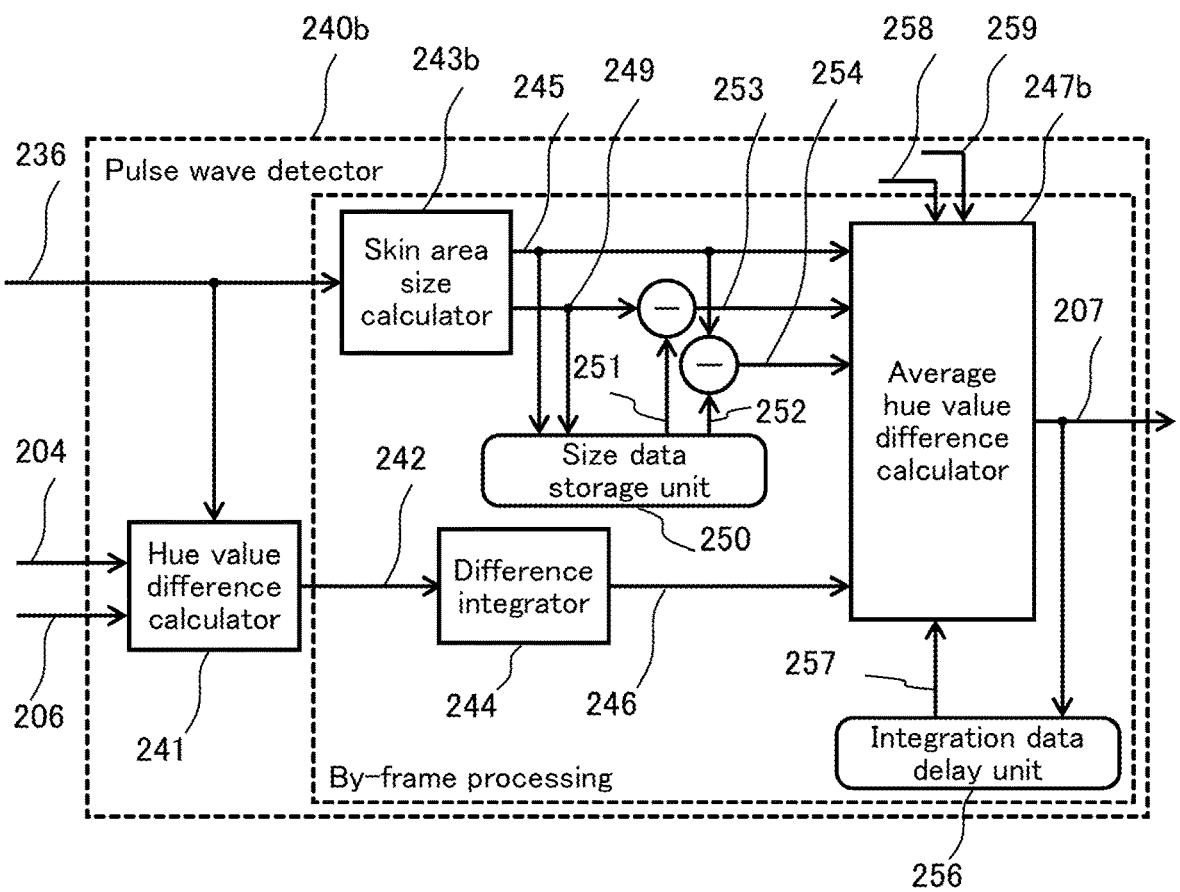
FIG. 15 is a block diagram to show details of an example configuration of a pulse wave detector adaptive to variation in external light.

FIG. 15 is a block diagram to show details of an example configuration of a pulse wave detector 240*b* adaptive to variation in external light. The pulse wave detector 240*b* includes the hue value difference calculator 241, a skin area size calculator 243*b*, a size data storage unit 250, the difference integrator 244, an integration data delay unit 256, and an average hue value difference calculator 247*b*, as shown in FIG. 15.

Here, the functions of the hue value difference calculator 241 and the difference integrator 244 are the same as those of the hue value difference calculator 241 and the difference integrator 244 of the pulse wave detector 240 in FIG. 11. That is, the hue value difference calculator 241 calculates a difference between frames on the hue information 204 on the skin area, and outputs hue difference information 242. In addition, the difference integrator 244 inputs the hue difference information 242, integrates the values of the hue difference information 242 on the pixels in the skin area, and outputs the integrated value as the integrated hue difference information 246.

In contrast, the functions of the skin area size calculator 243*b* and the average hue value difference calculator 247*b* are slightly different from those of the skin area size calculator 243 and the average hue value difference calculator 247 in FIG. 11.

The skin area size calculator 243*b* inputs the skin area indication information 236 outputted from the blood flow analysis unit 220*b* in FIG. 14, counts the number of pixels in the skin area, outputs the skin area size information 245 indicating the area of the skin area, and sums pieces of the value information 228 as the skin area indication information 236 to output the result as skin area value information 249 indicating the value of the skin area.

The size data storage unit 250 inputs and stores the skin area size information 245 and the skin area value information 249 on each frame, and outputs delayed skin area size information 252 and delayed skin area value information 251.

The integration data delay unit 256 temporarily stores the values of the pulse wave information 207 outputted from the average hue value difference calculator 247*b* for a plurality of frames, and outputs delayed pulse wave information 257 which is the pulse wave information 207 for the preceding plurality of frames.

The average hue value difference calculator 247*b* inputs the skin area size information 245 and the integrated hue difference information 246, and outputs a value obtained by dividing the value of the integrated hue difference information 246 by the value of the skin area size information 245, as the pulse wave information 207. The function of the average hue value difference calculator 247*b* is the same as that of the average hue value difference calculator 247 in FIG. 11. However, the average hue value difference calculator 247*b* has the following additional functions.

The difference skin area value information 253 inputted to the average hue value difference calculator 247*b* is a difference between the skin area value information 249 on the current frame and the skin area value information 249 on the frame preceding (e.g., immediately preceding) the current frame (that is, the delayed skin area value information 251 retrieved from the size data storage unit 250). Accordingly, the larger the difference skin area value information 253 is, the greater the change in value of the skin area between frames is.

Likewise, difference skin area size information 254 inputted to the average hue value difference calculator 247*b* is a difference between the skin area size information 245 of the current frame and the skin area size information 245 on the frame preceding (e.g., immediately preceding) the current frame (that is, the delayed skin area size information 252 retrieved from the size data storage unit 250). Accordingly, the larger the difference skin area size information 254 is, the larger the change in size of the skin area is.

It is assumed here that a sudden change has occurred in the external light received by the living body to be captured. In such a case, the difference skin area value information 253 is considered to change more than the difference skin area size information 254. Alternatively, the difference skin area size information 254 is considered to increase rapidly.

The average hue value difference calculator 247*b* is thus assumed to input the difference skin area value information 253, the difference skin area size information 254, a value difference threshold 258, and a skin area size difference threshold 259, in addition to the skin area size information 245 and the integrated hue difference information 246, and execute output processing. Here, the value difference threshold 258 and the skin area size difference threshold 259 are both preset constant values.

When the difference skin area value information 253 is larger than the value difference threshold 258, the average hue value difference calculator 247*b* outputs the delayed pulse wave information 257, which is the pulse wave information on the past (e.g., immediately preceding) frame, as the pulse wave information 207. Alternatively, the average value of the pulse wave information and delayed pulse wave information 257 calculated for the current frame is outputted as the pulse wave information 207.

Likewise, when the difference skin area size information 254 is larger than the skin area size difference threshold 259, the average hue value difference calculator 247b outputs the delayed pulse wave information 257, which is the pulse wave information on the past (e.g., immediately preceding) frame, as the pulse wave information 207. Alternatively, the average value of the pulse wave information and delayed pulse wave information 257 calculated and outputted for the current frame is outputted as pulse wave information 207.

With the above-described functions, the biological information detection device is capable of reducing a sudden change in the pulse wave information 207, even if the value or size of the skin area suddenly changes due to a sudden change in external light, to allow for reducing degradation in detection accuracy and erroneous detection, when detecting biological information such as the blood pressure and the heart rate.

Next, a description is given in detail of processing by the pulse wave propagation velocity calculation unit 302 (see FIG. 1) of the biological information detection device. As described above, the pulse wave propagation velocity calculation unit 302 calculates the pulse wave propagation velocity 303 from the pulse information 301 at the three skin areas of the forehead surface 20, the right buccal surface 21a, and the left buccal surface 21b, and the function is described in detail below.

Figure 16A:
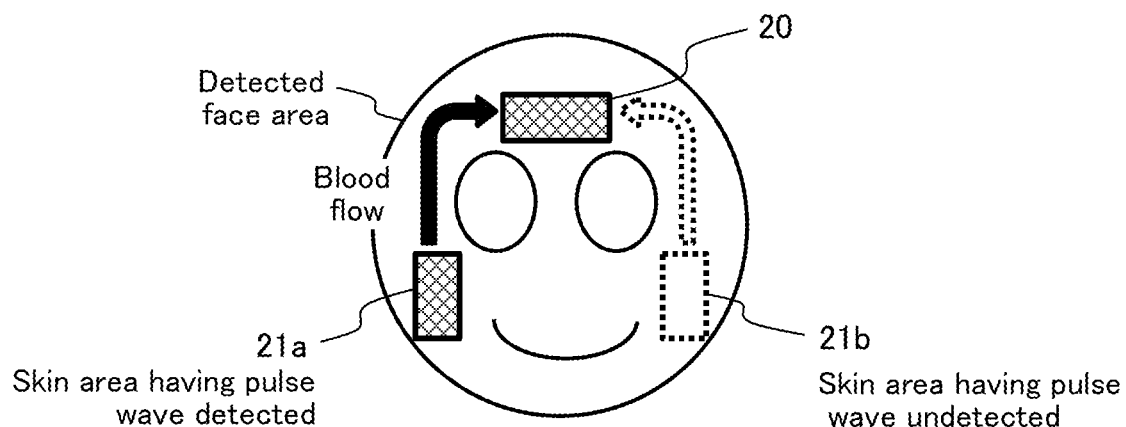
FIG. 16A illustrates processing when pulse wave detection partially fails.
Figure 16B:
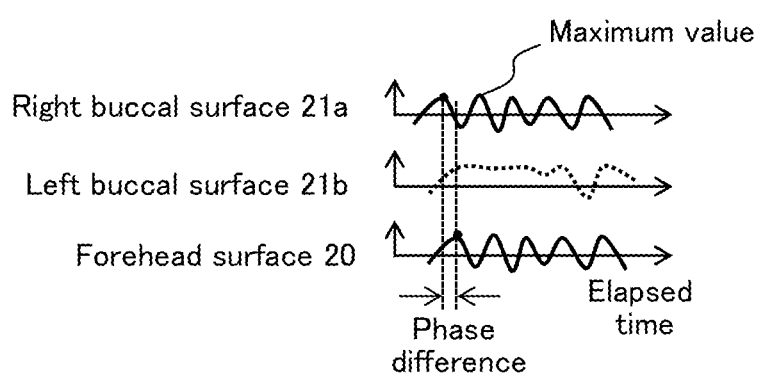
FIG. 16B shows pulse waves when pulse wave detection partially fails.

First, a description is given of processing in a case of partial failure in pulse wave detection, where a pulse wave has been undetected at the left buccal surface 21b, using FIGS. 16A and 16B. FIG. 16A illustrates a case of detecting pulse waves at the three skin areas of the forehead surface 20, the right buccal surface 21a, and the left buccal surface 21b, as in FIG. 3A, but failing to have the pulse wave detected at the left buccal surface 21b.

FIG. 163 shows pulse waves detected by the local pulse wave detection unit 400 at the respective skin areas of the forehead surface 20, the right buccal surface 21a, and the left buccal surface 21b. FIG. 16B shows that a pulse wave has been undetected at the left buccal surface 21b.

The pulse wave propagation velocity calculation unit 302 executes the process shown in FIG. 17, even when the pulse wave detection has partially failed as in FIG. 163, to calculate the pulse wave propagation velocity 303 from the pulse information 301 at the forehead surface 20 and the pulse information 301 at the right buccal surface 21a.

FIG. 17 is a flowchart of processing by the pulse wave propagation velocity calculation unit 302. In step S171, the pulse wave propagation velocity calculation unit 302 obtains pieces of the pulse information 301 detected by the local pulse wave detection units 400 at the respective skin areas of the forehead surface 20, the right buccal surface 21a, and the left buccal surface 21b.

In step S172, the pulse wave propagation velocity calculation unit 302 determines whether or not the obtained pulse information 301 at the forehead surface 20 is valid. The determination is made based on whether or not the pulse information 301 includes extremum information (sign for change in gradient). If the pulse information 301 at the forehead surface 20 is invalid (No in S172), the process ends because a phase difference between pulse waves cannot be calculated. If the pulse information 301 at the forehead surface 20 is valid (Yes in S172), processing proceeds to step S173.

In step S173, the pulse wave propagation velocity calculation unit 302 determines whether or not the pulse information 301 at the right buccal surface 21a and left buccal surface 21b obtained in step S171 is valid. The determination is made based on whether or not the pulse information 301 includes extremum information (sign for change in gradient). If the pulse information 301 at the right buccal surface 21a is valid and the pulse information 301 at the left buccal surface 21b is valid, processing proceeds to step S174. If the pulse information 301 at the right buccal surface 21a is invalid and the pulse information 301 at the left buccal surface 21b is valid, processing proceeds to step S177. If the pulse information 301 at the right buccal surface 21a is valid and the pulse information 301 at the left buccal surface 21b is invalid, processing proceeds to step S178. The processing in the case of partial failure in pulse wave detection shown in FIG. 16A is that of proceeding to step S178.

In step S174, the pulse wave propagation velocity calculation unit 302 calculates a phase difference in pulse waves from the pulse information 301 at the forehead surface 20 and the pulse information 301 at the right buccal surface 21a, and proceeds to step S175. In step S175, the pulse wave propagation velocity calculating unit 302 calculates a phase difference in pulse waves from the pulse information 301 at the forehead surface 20 and the pulse information 301 at the left buccal surface 21b, and proceeds to step S176. In step S176, the pulse wave propagation velocity calculation unit 302 averages the phase difference in pulse waves calculated in step S174 and the phase difference in pulse waves calculated in step S175, and then proceeds to step S179.

In step S177, the pulse wave propagation velocity calculation unit 302 calculates a phase difference in pulse waves from the pulse information 301 at the forehead surface 20 and the pulse information 301 at the left buccal surface 21b, and proceeds to step S179. In step S178, the pulse wave propagation velocity calculation unit 302 calculates a phase difference in pulse waves from the pulse information 301 at the forehead surface 20 and the pulse information 301 at the right buccal surface 21a, and proceeds to step S179.

In step S179, the pulse wave propagation velocity calculation unit 302 calculates a pulse wave propagation velocity based on the phase difference in pulse waves calculated in step S177, step S176, or step S178, and ends the process.

According to the processing flow of the pulse wave propagation velocity calculation unit 302 described above, the pulse wave propagation velocity is calculated based on detected pieces of the pulse information 301, even when the pulse wave detection has partially failed such that the pulse information 301 at the right buccal surface 21a or the left buccal surface 21b has been undetected.

In the biological information detection device as described above, a description has been given of a case where three skin areas of the forehead surface 20, the right buccal surface 21a, and the left buccal surface 21b are provided. However, the present invention is not limited thereto and skin areas of larger number of face surface portions may be provided to detect pieces of pulse wave information at respective skin areas for detecting a pulse rate and blood pressure value. In this case, the biological information detection device includes the local pulse wave detection units 400 for the number of provided skin areas, and the pulse wave propagation velocity calculation unit 302 obtains pieces of pulse information 301 from the respective local pulse wave detection units 400 for the number of skin areas, to calculate the pulse wave propagation velocity 303.

Figure 18A:
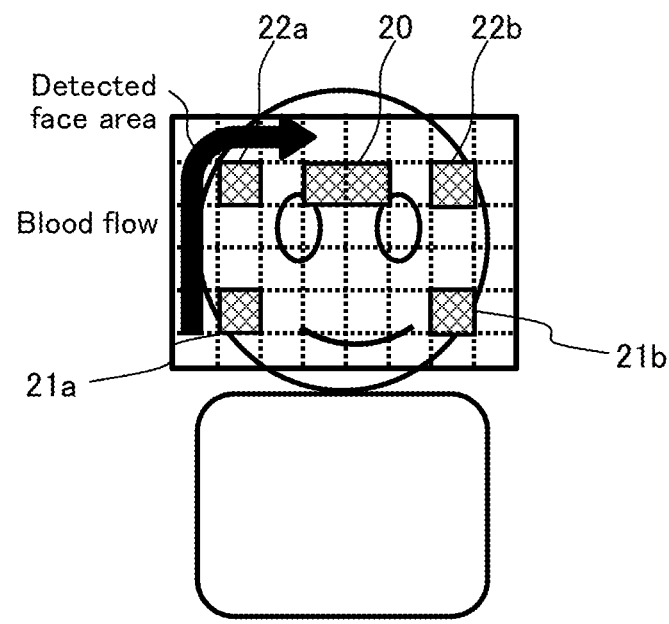
FIG. 18A shows a case of detecting a pulse wave propagation velocity based on five skin areas.

FIGS. 18A and 188 show a case of the biological information detection device detecting a pulse wave propagation velocity, based on five skin areas after face detection. In FIG. 18A, a right temple surface 22a and a left temple surface 22b are provided in addition to the three skin areas of the forehead surface 20, the right buccal surface 21a, and the left buccal surface 21b in FIG. 4, to have five skin areas, and pulse waves at the respective skin areas are detected.

Specifically, as shown in FIG. 18A, the right temple surface 22a is a skin area for a portion where the blood flow in FIG. 2, branched from the right external carotid artery to the superficial temporal artery and flowing to the frontal branch of the superficial temporal artery, flows through. That is, the blood flow at the right temple surface 22a becomes a blood flow in the middle of the blood vessel reaching the forehead surface 20. Likewise, the left temple surface 22b is a skin area for a portion where the blood flow in FIG. 2, branched from the left external carotid artery to the superficial temporal artery and flowing to the frontal branch of the superficial temporal artery, flows through for detecting a blood flow in the middle of the blood vessel reaching the forehead surface 20.

The skin areas of the right temple surface 22a and the left temple surface 22b are specified with a technique of specifying a range in the color space of the skin area (partial color space) as illustrated in FIG. 7, a technique of specifying area information (relative position from the reference, the area width, the area height) on the right temple surface 22a and the left temple surface 22b with reference to positions in the face area as illustrated in FIGS. 8A and 8B, or a technique of specifying area information (relative position from the reference, the area width, the area height) on the right temple surface 22a and the left temple surface 22b with reference to positions of characteristic portions in the face area (such as eyes) as illustrated in FIGS. 9A and 9B.

Figure 18B:
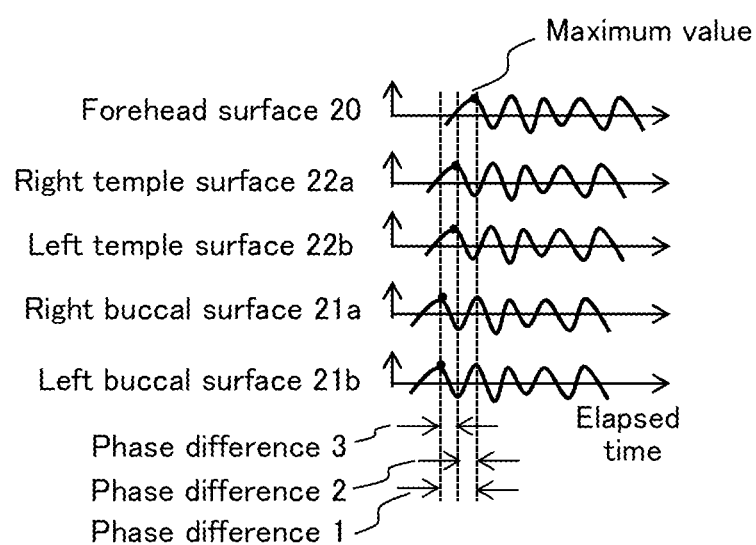
FIG. 18B shows pulse waves in the case of detecting the pulse wave propagation velocity based on the five skin areas.

FIG. 18B shows phase relationships between respective pieces of the pulse information 301 (pulse wave information 207) at the forehead surface 20, the right temple surface 22a, the left temple surface 22b, the right buccal surface 21a, and the left buccal surface 21b shown in FIG. 18A. The right temple surface 22a and the left temple surface 22b are skin areas in the middle of the blood vessel reaching the forehead surface 20, as described above, and thus the maximum values (peaks) in waveforms of the blood flow at the right temple surface 22a and the left temple surface 22b chronologically precede that at the forehead surface 20.

That is, a ratio of the phase difference between the right temple surface 22a and the forehead surface 20 to the phase difference between the right buccal surface 21a and the forehead surface 20 is substantially constant. Likewise, a ratio of the phase difference between the left temple surface 22b and the forehead surface 20 to the phase difference between the left buccal surface 21b and the forehead surface 20 is also substantially constant. The ratios of the phase difference for the right temple surface 22a and the left temple surface 22b indicate levels of the phase difference for the right temple surface 22a and the left temple surface 22b.

The pulse wave propagation velocity calculation unit 302 then determines that the ratio of the phase difference for the right temple surface 22a and the left temple surface 22b does not change significantly (the amount of change in the ratio of the phase difference is within a predetermined threshold), or the ratio of the phase difference falls within a predetermined range, to determine that there is no abnormality in detecting the pulse waves at the skin areas, and calculates the pulse wave propagation velocity. This improves accuracy in calculating the pulse wave propagation velocity.

FIG. 19 is a flowchart of processing by the pulse wave propagation velocity calculation unit 302 in a case where the pulse wave propagation velocity is detected based on the five skin areas in FIG. 18A. In step S191, the pulse wave propagation velocity calculation unit 302 obtains pieces of the pulse information 301 detected by the local pulse wave detection units 400 at the respective skin areas of the forehead surface 20, the right buccal surface 21a, the left buccal surface 21b, the right temple surface 22a, and the left temple surface 12b.

In step S192, the pulse wave propagation velocity calculation unit 302 calculates a phase difference "a" in pulse waves, based on the pulse information 301 at the right buccal surface 21a and the pulse information 301 at the forehead surface 20, and based on the pulse information 301 at the left buccal surface 21b and the pulse information 301 at the forehead surface 20, respectively, and proceeds to step S193.

In step S193, the pulse wave propagation velocity calculation unit 302 calculates a phase difference "b" in pulse waves, based on the pulse information 301 at the right temple surface 22a and the pulse information 301 at the forehead surface 20, and based on the pulse information 301 at the left temple surface 22b and the pulse information 301 at the forehead surface 20, respectively, and proceeds to step S194.

In step S194, the pulse wave propagation velocity calculation unit 302 calculates a phase difference "c" in pulse waves, based on the pulse information 301 at the right buccal surface 21a and the pulse information 301 at the right temple surface 22a, and based on the pulse information 301 at the left buccal surface 21b and the pulse information 301 at the left temple surface 22b, respectively, and proceeds to step S195.

In step S195, the pulse wave propagation velocity calculation unit 302 calculates an amount of a temporal change in a level of the phase difference for the right temple surface 22a and the left temple surface 22b, based on the ratio of the phase difference "b" in pulse waves calculated in step S193 to the phase difference "a" in pulse waves calculated in step S192, or based on the ratio of the phase difference "c" in pulse waves calculated in step S194 to the phase difference "a" in pulse waves calculated in step S192.

In step S196, the pulse wave propagation velocity calculation unit 302 determines whether or not the amount of a change in a level of the phase difference for the right temple surface 22a and the left temple surface 22b calculated in step S195 falls within a predetermined threshold. If the amount of a change fails to fall within the predetermined threshold (No in S196), the process ends as a case where detecting the pulse waves at the skin areas has not been successfully completed. If the amount of a change falls within the predetermined threshold (Yes in S196), the process proceeds to step S197.

In step S197, the pulse wave propagation velocity calculation unit 302 calculates the pulse wave propagation velocity based on the pulse wave phase difference "a" calculated in step S192, and ends the process.

As described above, the pulse wave propagation velocity calculation unit 302 calculates the pulse wave propagation velocity, taking into account the relative fluctuation in the blood flow information detected at the skin areas, to avoid abnormal detection and calculate the pulse wave propagation velocity accurately with less error.

Hereinabove the biological information detection device has been described in a case of calculating the pulse wave propagation velocity from the video information of the reflected light at the skin areas of a living body to estimate the blood pressure, but may calculate information on a phase difference between the skin areas, as biological information, based on pieces of the pulse information 301 obtained for the respective skin areas, and use the biological information as individual identification information for biometric identification.

The present invention is not limited to the above-described embodiment, and includes various modifications. The above embodiment has been described in detail for the purpose of illustrating the present invention, and are not necessarily limited to those having all the configurations described above. In addition, a part of a configuration of one embodiment can be replaced with a configuration of another embodiment, and the configuration of another embodiment can be added to the configuration of one embodiment.

LEGEND FOR REFERENCE NUMERALS

20: forehead surface (skin area), 21a: right buccal surface (skin area), 21b: left buccal surface (skin area), 22a: right temple surface, 22b: left temple surface, 100: camera, 101: video signal, 103: blood pressure value output unit, 201: video capture unit, 202: video data, 203: skin area indication information, 204: blood flow information (hue information), 205: frame delay unit, 207: pulse wave information, 220: blood flow analysis unit, 220b: blood flow analysis unit, 221: video data storage unit, 222: delayed video data, 223: spatial filter, 224: smoothed video data, 225: unpacked information, 226: HSV conversion unit, 227: saturation information, 228: value information, 229: skin area detection unit, 230: face detection unit, 231: face area information, 233: selection information, 234: area count parameter, 235: area divider, 236: skin area indication information, 240: pulse wave detector, 240b: pulse wave detector, hue value difference calculator, 242: hue difference information, 243: skin area size calculator, 243b: skin area size calculator, 244: difference integrator, 245: skin area size information, 246: integrated hue difference information, 247: average hue value difference calculator, 247b: average hue value difference calculator, 249: skin area value information, 250: size data storage unit, 251: delayed skin area value information, 252: delayed skin area size information, 253: difference skin area value information, 254: difference skin area size information, 256: integration data delay unit, 257: delayed pulse wave information, 258: value difference threshold, 259: skin area size difference threshold, 260: pulse detector, 261: difference data storage unit, 262: delayed pulse wave information, 263: smoothing filter, 264: smoothed pulse wave information, 265: smoothed data delay unit, 266: delayed smoothed pulse wave information, 267: gradient detector, 268: gradient information, 269: code data delay unit, 270: delayed gradient information, 271: extremum detector, 290: selector, 301: pulse information, 302: pulse wave propagation velocity calculation unit, 303: pulse wave propagation velocity, 304: blood flow information, 320: blood pressure estimation unit, 321: pulse wave propagation velocity delaying unit, 322: smoothing filter, 323: smoothed pulse wave propagation velocity, 324: blood pressure correction parameter, 325: blood pressure corrector, 326: blood pressure conversion table, 327: delayed pulse wave propagation velocity, 328: blood pressure conversion information, and 400a, 400b, 400c: local pulse wave detection unit.

The invention claimed is:

1. A biological information detection device comprising:
a video capture unit to obtain video information having a face of a living body captured;
a blood flow analysis unit to analyze video data of at least three skin areas in the video information, as blood flow information, inclusive of a skin area located on a center line of the face and a pair of skin areas, which is located bilaterally symmetric to the center line and has a blood flow path closer to the heart than the skin area located on the center line;
a local pulse wave detection unit provided for each skin area to calculate pulse information at the skin area based on the blood flow information sequenced chronologically;
a pulse wave propagation velocity calculation unit to calculate a pulse wave propagation velocity based on a phase difference between pieces of the pulse information at each of the skin areas calculated by the local pulse wave detection unit; and
a blood pressure estimation unit to estimate blood pressure based on the pulse wave propagation velocity, wherein
the blood flow analysis unit obtains pieces of hue information on respective pixels of the video data corresponding to the at least three skin areas, and
the local pulse wave detection unit obtains differences in the hue information between frames, integrates the differences to obtain an integrated value, calculates an average hue difference value using a size of the skin area and the integrated value to obtain pulse wave information, and chronologically obtains an extremum of the pulse wave information, which is then added to the pulse wave information to have the pulse information.

2. The biological information detection device as claimed in claim 1, wherein
the blood flow analysis unit uses video data in the video information within a specified range in a color space, as the video data of the at least three skin areas.

3. The biological information detection device as claimed in claim 2, wherein
the blood flow analysis unit uses video data in face-detected video information within a specified range in the color space, as the video data of the at least three skin areas.

4. The biological information detection device as claimed in claim 1, wherein
the blood flow analysis unit uses video data in the video information within a range having an area position specified with reference to a face-detected face area, or within a range having an area position specified with reference to characteristic portions of the face.

5. The biological information detection device as claimed in claim 1, wherein
the blood flow analysis unit further obtains value information on respective pixels of the video data corresponding to the at least three skin areas, and
the local pulse wave detection unit integrates the value information on the skin areas to obtain an average value, and when a difference in the average value between frames is larger than a predetermined value, sets the average hue difference value of a frame preceding the current frame as blood wave information, or sets an average of the average hue difference value of the frame preceding the current frame and the average hue difference value of the current frame as the blood wave information.

6. The biological information detection device as claimed in claim 1, wherein
the local pulse wave detection unit, when a difference in a size of the skin area between frames is larger than a predetermined value, sets the average hue difference value of a frame preceding the current frame as pulse wave information, or sets an average of the average hue difference value of the frame preceding the current frame and the average hue difference value of the current frame as the blood wave information.

7. The biological information detection device as claimed in claim 1, wherein
the at least three skin areas are areas at a forehead surface, a right buccal surface, and a left buccal surface, and
the pulse wave propagation velocity calculation unit calculates a pulse wave propagation velocity from a phase difference between pulse information at the forehead surface and pulse information at the right buccal surface, or a phase difference between pulse information at the forehead surface and pulse information at the left buccal surface.

8. The biological information detection device as claimed in claim 1, wherein
the at least three skin areas are areas at a forehead surface, a right buccal surface, a left buccal surface, a right temple surface, and a left temple surface, and
the pulse wave propagation velocity calculation unit calculates a pulse wave propagation velocity from a phase difference between pulse information at the forehead surface and pulse information at the right buccal surface, when a phase of the pulse information at the right temple surface is at a predetermined position with respect to phases of the pulse information at the forehead surface and the right buccal surface, or from a phase difference between pulse information at the forehead surface and pulse information at the left buccal surface, when a phase of the pulse information at the left temple surface is at a predetermined position with respect to phases of the pulse information at the forehead surface and the left buccal surface.

9. A biological information detection method used for a biological information detection device to detect a blood flow from video information having a face of a living body captured to estimate blood pressure, the method comprising:
storing a phase difference in pulse information and blood pressure, in association with each other, for at least three skin areas on the face in a normal state;
setting conditions for extracting video data of the skin areas to be extracted from the video information, by specifying ranges in a color space of the skin areas or specifying positions of the skin areas with reference to characteristic portions of the face;
extracting video data from the video information for each of the skin areas, based on the conditions for extracting video data, to output hue information on the video data as blood flow information;
calculating pulse information at each of the skin areas, based on a chronological change in the blood flow information;
obtaining a phase difference between pieces of the pulse information at the predetermined skin areas; and
estimating blood pressure corresponding to the phase difference between pieces of the pulse information, with reference to the stored phase differences in pulse information in association with blood pressure.

10. The biological information detection method as claimed in claim 9, wherein
the at least three skin areas are areas at a forehead surface, a right buccal surface, and a left buccal surface, and
at the time of obtaining a phase difference, a phase difference between pulse information at the forehead surface and pulse information at the right buccal surface, or a phase difference between pulse information at the forehead surface and pulse information at the left buccal surface is obtained.

11. The biological information detection method as claimed in claim 9, wherein
the at least three skin areas are areas at a forehead surface, a right buccal surface, a left buccal surface, a right temple surface, and a left temple surface, and
at the time of obtaining a phase difference, a phase difference between pulse information at the forehead surface and pulse information at the right buccal surface is obtained, when a phase of the pulse information at the right temple surface is at a predetermined position with respect to phases of the pulse information at the forehead surface and the right buccal surface, or a phase difference between pulse information at the forehead surface and pulse information at the left buccal surface is obtained, when a phase of the pulse information at the left temple surface is at a predetermined position with respect to phases of the pulse information at the forehead surface and the left buccal surface.

12. A non-transitory computer-readable medium for biological information detection to implement a biological information detection device that detects a blood flow from video information having a face of a living body captured to estimate blood pressure, the medium storing one or more computer programs, when executed by a processor, to execute steps comprising:
storing phase differences in pulse information on at least three skin areas on the face in a normal state in association with blood pressure at the skin areas;
setting conditions for extracting video data of the skin areas to be extracted from the video information, by specifying ranges in a color space of the skin areas or specifying positions of the skin areas with reference to characteristic portions of the face;
extracting video data from the video information for each of the skin areas, based on the conditions for extracting video data, to output hue information on the video data as blood flow information;
calculating pulse information at each of the skin areas, based on a chronological change in the blood flow information;
obtaining a phase difference between pieces of the pulse information at the predetermined skin areas; and
estimating blood pressure corresponding to the phase difference between pieces of the pulse information, with reference to the stored phase differences in pulse information in association with blood pressure.

13. The non-transitory computer-readable medium for biological information detection as claimed in claim 12, wherein
the at least three skin areas are areas at a forehead surface, a right buccal surface, and a left buccal surface, and
at the time of obtaining a phase difference, a phase difference between pulse information at the forehead surface and pulse information at the right buccal surface, or a phase difference between pulse information at the forehead surface and pulse information at the left buccal surface is obtained.

14. The non-transitory computer-readable medium for biological information detection as claimed in claim 12, wherein
the at least three skin areas are areas at a forehead surface, a right buccal surface, a left buccal surface, a right temple surface, and a left temple surface, and at the time of obtaining a phase difference, a phase difference between pulse information at the forehead surface and pulse information at the right buccal surface is obtained, when a phase of the pulse information at the right temple surface is at a predetermined position with respect to phases of the pulse information at the forehead surface and the right buccal surface, or a phase difference between pulse information at the forehead surface and pulse information at the left buccal surface is obtained, when a phase of the pulse information at the left temple surface is at a predetermined position with respect to phases of the pulse information at the forehead surface and the left buccal surface.

* * * * *

UNITED STATES PATENT AND TRADEMARK OFFICE
CERTIFICATE OF CORRECTION

| | |
|---|---|
| PATENT NO. | : 11,547,309 B2 |
| APPLICATION NO. | : 16/818189 |
| DATED | : January 10, 2023 |
| INVENTOR(S) | : Nobuhiro Fukuda et al. |

It is certified that error appears in the above-identified patent and that said Letters Patent is hereby corrected as shown below:

On the Title Page

In item (73), under "Assignee", delete "Hitachi, Ltd." and insert therefor --Hitachi, Ltd., Tokyo (JP)--.

Signed and Sealed this
Twenty-first Day of March, 2023

*Katherine Kelly Vidal*

Katherine Kelly Vidal
*Director of the United States Patent and Trademark Office*